United States Patent
Frassica

(10) Patent No.: US 6,379,334 B1
(45) Date of Patent: Apr. 30, 2002

(54) ROTATE ADVANCE CATHETERIZATION SYSTEM

(75) Inventor: James J. Frassica, Chelmsford, MA (US)

(73) Assignee: Essex Technology, Inc., Chelmsford, MA (US)

(*) Notice: Subject to any disclaimer, the term of this patent is extended or adjusted under 35 U.S.C. 154(b) by 0 days.

(21) Appl. No.: 09/448,054

(22) Filed: Nov. 23, 1999

Related U.S. Application Data

(63) Continuation of application No. 08/797,426, filed on Feb. 10, 1997, now Pat. No. 5,989,230.

(51) Int. Cl.[7] .............................................. A61M 5/178
(52) U.S. Cl. ........................... 604/165.04; 604/164.07; 604/165.01; 604/528
(58) Field of Search .................... 604/264, 523–524, 604/528, 915–916, 96.01, 103.06, 103.08, 103.09, 540, 541, 543, 544, 164.01, 164.07, 165.01, 165.04; 600/101, 109, 160, 129, 130, 114; 606/192–194, 1, 108, 198, 72–73

(56) References Cited

U.S. PATENT DOCUMENTS

| | | | |
|---|---|---|---|
| 207,932 A | * | 9/1878 | Alvord |
| 761,235 A | * | 5/1904 | Kepler |
| 1,644,919 A | * | 10/1927 | Hayes |
| 2,173,527 A | * | 9/1939 | Agayoff |
| 2,896,629 A | * | 7/1959 | Warr |
| 4,445,509 A | * | 5/1984 | Auth |
| 4,682,981 A | * | 7/1987 | Suzuki et al. |
| 4,762,130 A | * | 8/1988 | Fogarty et al. |
| 4,834,724 A | * | 5/1989 | Geiss et al. |
| 4,950,232 A | * | 8/1990 | Ruzicka et al. |
| 4,955,859 A | * | 9/1990 | Zilber |
| 5,009,643 A | * | 4/1991 | Reich et al. |
| 5,087,252 A | * | 2/1992 | Denard |
| 5,129,910 A | * | 7/1992 | Phan et al. |
| 5,246,441 A | * | 9/1993 | Ross et al. ..................... 606/53 |
| 5,246,445 A | * | 9/1993 | Yachia et al. |
| 5,308,354 A | * | 5/1994 | Zacca et al. |
| 5,334,211 A | * | 8/1994 | Schiber |
| 5,456,685 A | * | 10/1995 | Huebner ........................ 606/73 |
| 5,672,158 A | * | 9/1997 | Okada et al. |

OTHER PUBLICATIONS

"Anatomy, Descriptibe & surgical" by Henry Gray, 1977 Crown Publisher pp. 98–1001,1004–1007,1026–1027.*
"Ancient Inventions", 1st Ed 1994 by Peter James & Nick Thorpe, Ballantine Books pp. 15 & 16.*
"Perspective inUrology", Hoffman–Larducue, 1976 Pub of AMerican Urological Assoc. pp. 117–134.*
"Antique Medical Instruments", by C. Keith Wilbur, M.D., Schiffer Pub Ltd., pp. 74–75.*
"Urology Productions", Bard Urological Div. 6 pages Product Data Sheets.*
"A Presentation of Catheters and Urological Specialties for . . ." 1 page Foley Catheters/Urological Specialties.*

* cited by examiner

*Primary Examiner*—Richard K. Seidel
*Assistant Examiner*—LoAn H. Thanh
(74) *Attorney, Agent, or Firm*—Pandiscio & Pandiscio

(57) ABSTRACT

A system of rotate-to-advance medical devices including catheters, dilators, occluders, stents, suprapubic catheters and camera introducers configured with external screw threads and depending substantially on rotation for means of advancement and emplacement in mammalian genitourinary and gastrointestinal passages and organs.

6 Claims, 12 Drawing Sheets

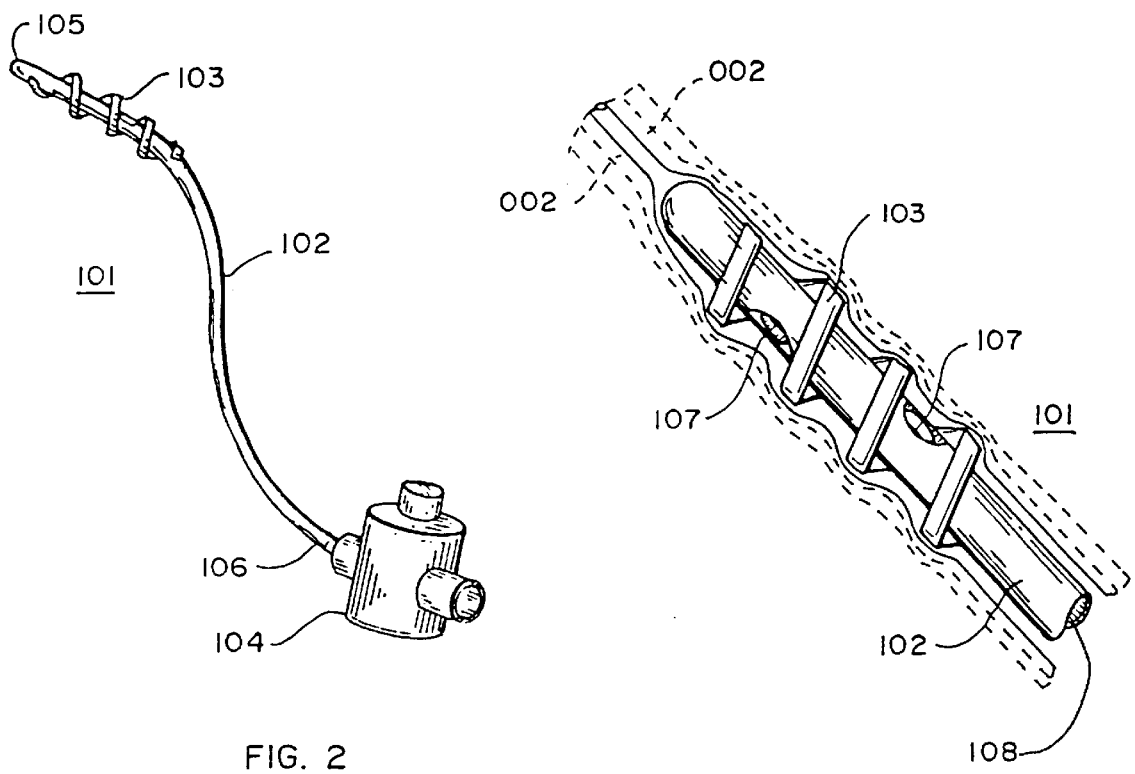
FIG. 2
FIG. 4
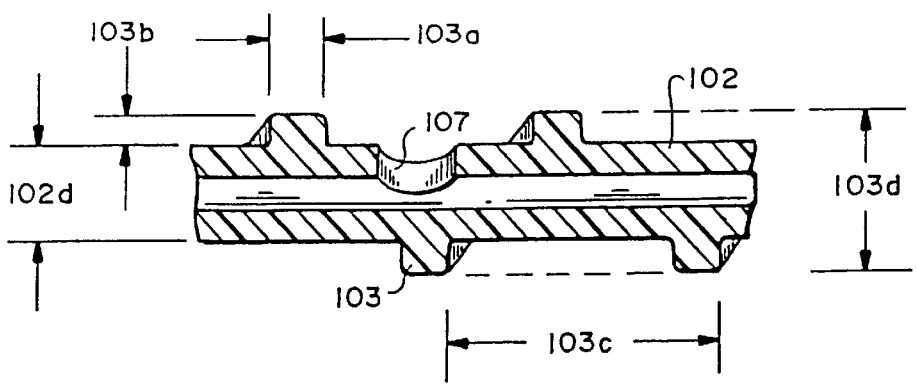
FIG. 3

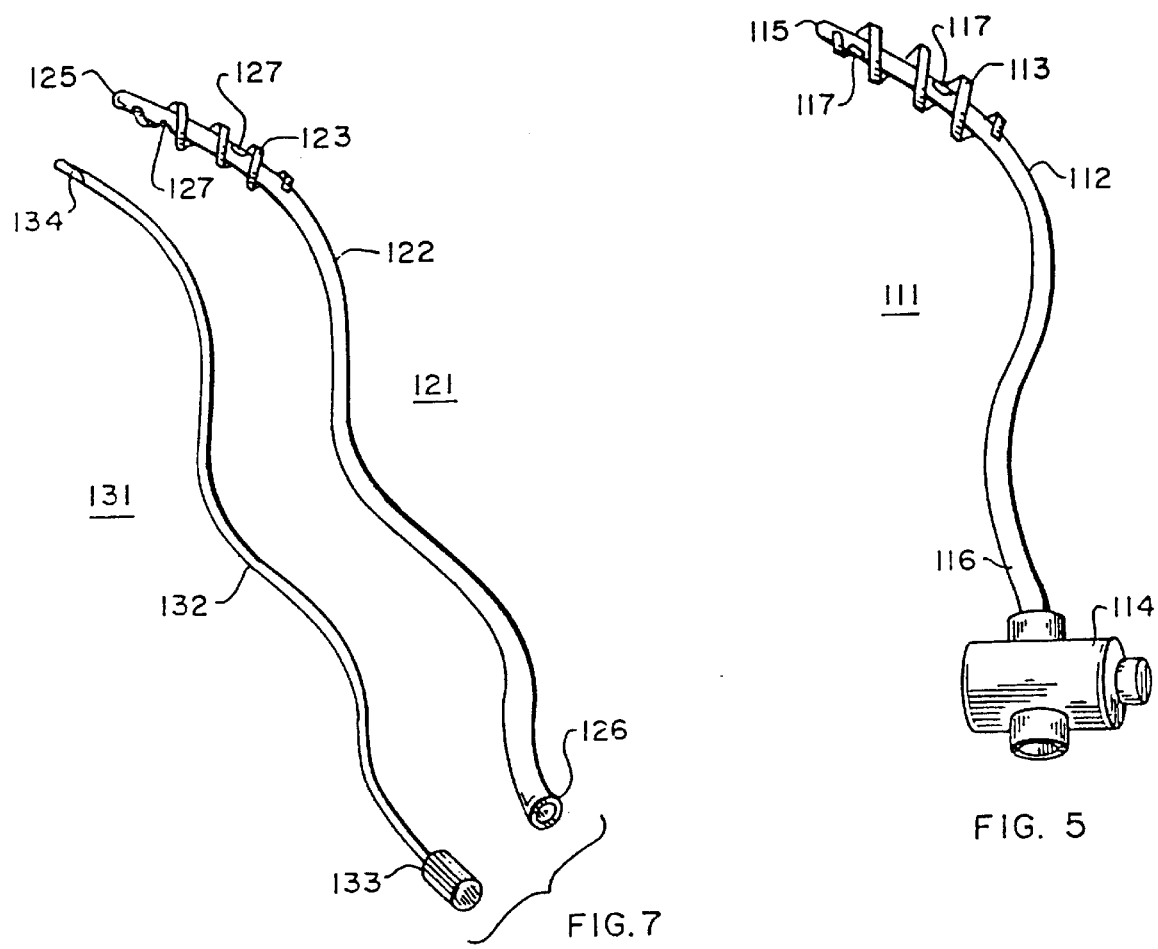
FIG. 7
FIG. 5
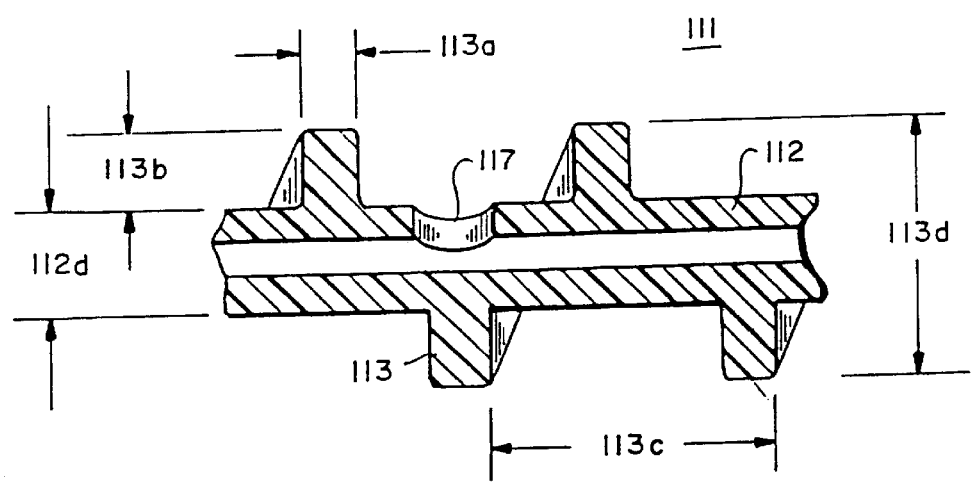
FIG. 6

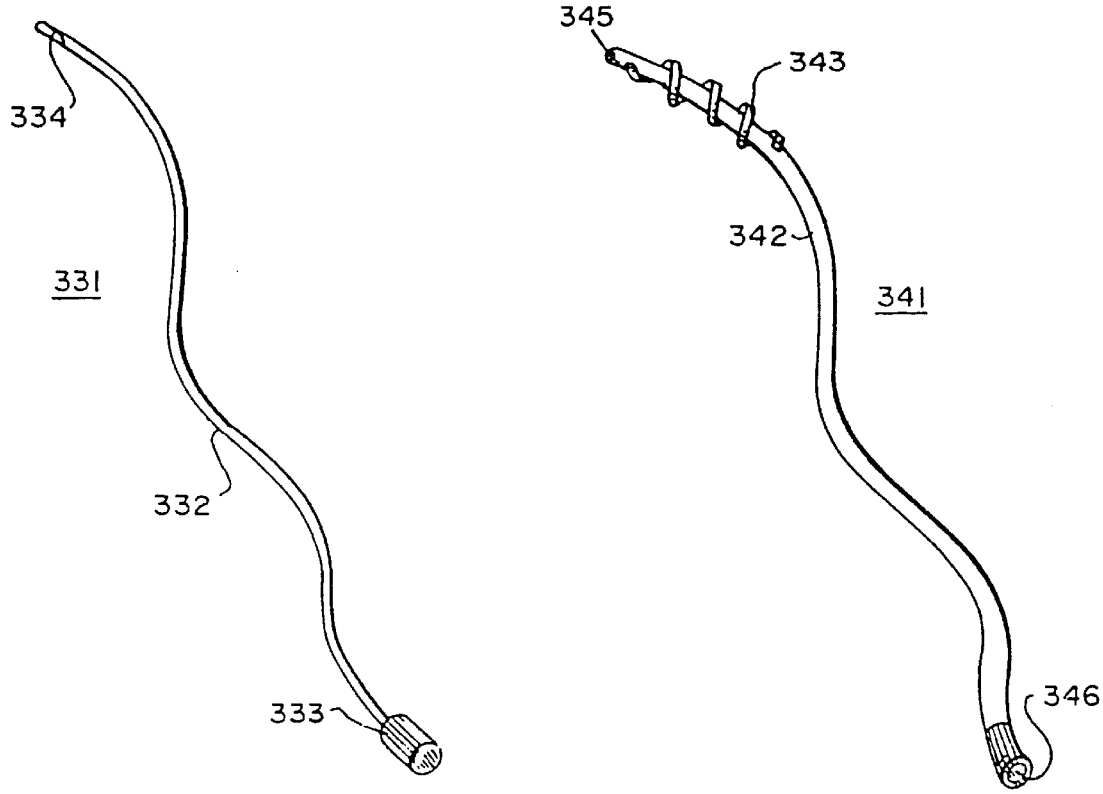
FIG. 19
FIG. 21
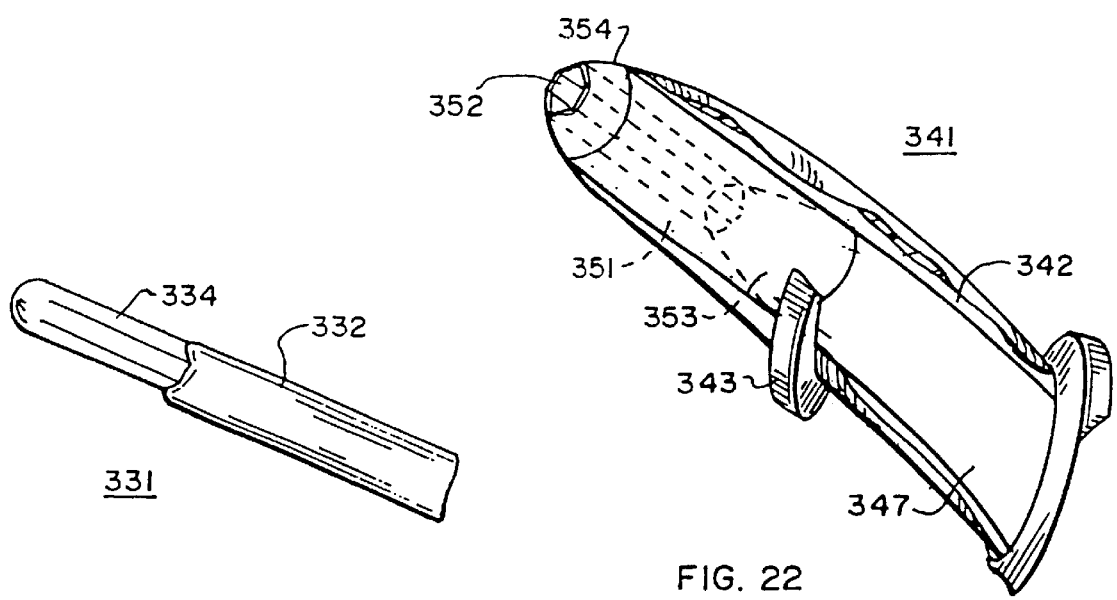
FIG. 20
FIG. 22

ROTATE ADVANCE CATHETERIZATION SYSTEM

This is a continuation of U.S. patent application Ser. No. 08/797,426, filed Feb. 10, 1997 now U.S. Pat. No. 5,989,230 by James J. Frassica for ROTATE TO ADVANCE CATHETERIZATION SYSTEM.

BACKGROUND OF THE INVENTION

1. Technical Field of the Invention

This invention most generally relates to apparatus and methods of catheterization and related treatments of the genitourinary and gastrointestinal passages of mammals. More particularly, the invention relates to catheters, dilators, occluders, stents, suprapubic catheters, camera introducers and related medical devices subject to being proximally propelled and directed for advancement and control in mammalian genitourinary and gastrointestinal passages.

2. Description of the Prior Art

In most mammals, mucous membranes line all those passages by which the internal parts communicate with the exterior, and are continuous with the skin at the various orifices of the surface of the body. They are soft and velvety, and very vascular, and their surface is coated over by their secretion, mucus, which is of a tenacious consistence, and serves to protect them from the foreign substances introduced into the body with which they are brought in contact.

They are described as lining the two tracts—the genitourinary and the gastrointestinal; and all, or almost all, mucous membranes may be classed as belonging to and continuous with the one or the other of these tracts. Catheterization of any of these similar bodily passages may at times be useful or necessary.

Urinary outlet problems most likely have been around for as long as humans. History has the ancient Chinese using onion stalks to relieve people of acute urinary retention.

Literature refers to such problems as far back as 206 B.C., more than 2000 years ago. Romans used catheters, first invented by Erasistratus, a Greek doctor in the third century B.C. Roman catheters were fine tubes made of bronze. The Roman gynecologist Soranus describes how catheters could be used to push stones out of the way and back into the cavity of the bladder, and thus restore urine flow. Excavations in Pompeii unearthed several bronze catheters. These instruments were well constructed but relatively simple and showed that designs changed little from the period 79 AD until 1700 A.D.

However, during the 17th and 18th centuries catheter construction became more complex with an intensified search for an appropriate substance that would be at once flexible, non-irritating and functional. England, France, and the U.S.A. had individuals and companies deeply involved with urinary catheters during this period. Many variations were produced but they all caused much stress on the patient when these rigid devices were pushed into the urethra. The first practical breakthrough was by the French using gum elastic catheters—a catheter that would bend better in the urethral channel and not scour the mucosa so much in the process.

Charles Goodyear improved upon what the French produced when he successfully vulcanized crude rubber. The problem of manufacturing an instrument which was both sufficiently rigid to enable it to be pushed through the urethra into the bladder and yet flexible enough to negotiate the path, had at last reached the point of practicality, not withstanding its shortcomings. At that time, and still to this day, a functional urethral catheter is defined as one that is flexible enough to negotiate the bends and stable enough to push through the length of the urethral passage.

The French urologist J. J. Cazenave, with the hopes that his country would regain leadership in the catheter field, dedicated 25–30 years of his life improving the flexible durable catheter. This was in the late 1800's and his catheter, made of decalcified ivory, was a dated device but shows the consistency of the state of the art wherein catheters are pushed into and negotiated along the urethral passage toward the bladder.

During the past 300 years or so, intensified development efforts were stimulated by professional pride, national pride and financial rewards. These efforts yielded many improvements, such as changes to size, curve shape, materials of construction, smoothness, lubricants, coatings, combinations of materials, physical properties, chemical properties and more, yet all subscribed to the basic principle of external push-to-advance.

The catheters of the prior art are large and stiff, difficult and uncomfortable to administer, and uncomfortable to wear for extended periods. There is a degree of skill, tolerance and patience required that takes much time, training and practice to learn. The difficulty, discomfort, risk of injury and infection, inhibition and inconvenience of the methods and tools of the known art results in the deprivation for many patients of the freedom to work, play and travel as do unaffected people.

The anatomy of the adult male urinary tract, as illustrated in FIG. 1, has a bladder 004 where urine is collected prior to exiting the body via the urethra 006. The bladder 004 converges into the urethra 006 at a muscular exit called the bladder neck 005. Approximately the first one inch of the urethra lies within the prostate 007, which is a chestnut-sized gland. The next approximately half inch passes through the external sphincter 008, which is the muscular flow valve that controls the release of urine. The remaining six inches of the urethra lie in a spongy zone, exiting the body at the meatus 009.

The normal process of emptying the bladder can be interrupted by two causes. One is bladder outlet obstruction and the other is failure of the nerves linking the bladder to the brain. The most frequent cause of bladder outlet obstruction in males is enlargement of the prostate gland by hypertrophy or hyperplasia. In older males, it is not uncommon for a progressive enlargement of the prostate to constrict the prostate urethra. This condition, known as benign prostatic hyperplasia (BPH), can cause a variety of obstructive symptoms, including urinary hesitancy, straining to void, decreased size and force of the urinary stream and in extreme cases, complete urinary retention possibly leading to renal failure.

The most common surgical intervention for BPH, transurethral resection of the prostate, or TURP, has a lengthy recovery period of up to one year, and presents a high operative risk for complications such as sexual dysfunction. Up to 10% of those subjected to such surgery are left with mild to moderate stress incontinence. Approximately 400,000 patients in the United States and approximately 500,000 patients internationally were diagnosed in 1994 with BPH or cancer-induced bladder outlet obstructions that were sufficiently severe to warrant TURP or alternative surgery, according to industry sources.

Because of the high costs, medical risks and quality of life compromises associated with TURP, new technologies have begun to challenge TURP's position as the standard treatment for severe BPH. Recently, the U.S. Food and Drug Administration approved two drugs, tera zosin hydrochloride and rinasteride, to treat BPH. These drugs generally do not improve symptoms for six to nine months after treatment begins, and are not without side effects.

Urethral strictures are another cause of outlet obstruction, often due to fibrous tissue growth resulting from reaction to catheters or cystoscopes or from injury, birth defects or disease, and are commonly treated by urethral dilation, catheterization or surgery. Men with urethral strictures also experience a limited ability to urinate, which may cause extreme discomfort and, if left untreated may cause complications that necessitate catheterization. Approximately 50,000 patients in the United States were diagnosed with recurrent urethral strictures in 1994, according to industry sources. The inventor estimates that approximately 75,000 additional patients were diagnosed internationally.

Women suffer from urinary incontinence far more often than men and at an younger age primarily because of the stress associated with pregnancy and childbirth, the shorter length of the female urethra, and the absence of a prostate. The U.S. Department of Health and Human Services (HHS) estimates that the involuntary loss of urine affects approximately 10 million Americans of which 8.5 million are women. Seven million of these women are non-institutionalized, or community-dwelling.

For women between the ages of 15 and 64, the prevalence of urinary incontinence is estimated to range from 10 to 25 percent of the population. For non-institutionalized persons over the age of 60, the prevalence of urinary incontinence ranges from 15 to 30 percent, with the prevalence in women twice that of men.

The involuntary loss of urine can be caused by a variety of anatomical and physiological factors. The type and cause of urinary incontinence is important to how the condition is treated and managed. The two broad categories of urinary incontinence are urge and stress incontinence. Some people suffer from what is termed mixed incontinence or a combination of stress and urge incontinence.

Urge incontinence is the involuntary loss of urine associated with an abrupt and strong desire to void. In most cases, urge incontinence is caused by involuntary detrusor (the smooth muscle in the wall of the bladder) contractions or over-activity. For many people, urge incontinence can be satisfactorily managed with pharmaceuticals.

The more frequently occurring stress incontinence is the involuntary loss of urine caused by movement or activity that increases abdominal pressure. The most common cause of stress incontinence is hypermobility or significant displacement of the urethra and bladder neck during exertion. A less frequent cause of stress incontinence is intrinsic urethral sphincter deficiency (ISD), a condition in which the sphincter is unable to generate enough resistance to retain urine in the bladder.

Females, and males with no benign prostatic hyperplasia condition, might also have the inability to empty their bladder because of the nerves linking the bladder to the brain. This condition is known as neuropathic bladder, may occur in a wide variety of conditions which include spina bifida, multiple sclerosis, spinal injury, slipped disc and diabetes. When these and other problems prevent the bladder from effectively controlling urine there are a number of treatment options. They are catheters, dilators, occluders, and stents.

Indwelling Foley-type Catheters

During continuous catheterization an indwelling catheter is retained in the bladder by a water filled balloon. It drains urine continuously from the bladder via a connecting tube into a bag which is attached to the leg or bed. The bag has a tap so that the urine can be emptied at intervals. The catheter is usually inserted by a doctor or nurse and changed about every four to six weeks. But difficulty in placement has always been inherent in this design. This is due to the traditional "push to advance" technology which necessitates a relatively stiff, thick-walled catheter to traverse the delicate mucosal lined urethra.

Often the French (unit of measurement) size of the catheter is dictated by the need for stiffness to insert rather than the lumen size to pass urine. A 14 French or smaller Foley is rarely used because catheters of this size lack the column strength needed to push the full length of the urethra into the bladder. The larger French Foley catheters are painful to place, uncomfortable when indwelling, and require a highly skilled care provider to insert.

Intermittent Catheters

During intermittent catheterization a simple catheter made of plastic, rubber, or metal is inserted by the patient or a helper for just long enough to empty the bladder completely, which is typically about one minute. These tubes are usually smaller in diameter and stiffer than an indwelling catheter of the same size. This stiffness can make catheterization difficult in men because the urethra is long and has an acute bend within the prostate. When the external sphincter is reached the sphincter muscle will contract making passage difficult.

Most patients learn to catheterize themselves and thereby gain a large degree of independence. This process is repeated about every 3–4 hours during the day and occasionally as needed at night.

Intermittent catheterization is mainly used by people who are incontinent due to neuropathic bladder. Intermittent catheterization may also be utilized by people who cannot empty the bladder because the bladder muscle is weak and does not contract properly. In some patients, an alternate apparatus and method used to maintain long term drainage of the bladder is the use of a suprapubic tube.

Suprapubic Catheters

Suprapubic catheterization of the bladder is performed via transabdominal puncture which enters the body above the pubic arch and is directed into the bladder using ultrasound or fluoroscopy to guide the trocar introducer and suprapubic catheter. The needle introducer is then removed when proper catheter placement within the bladder is confirmed, leaving the drainage catheter in place.

Long term drainage may require the fixation of the catheter at the skin using standard adhesive based interface components to address mechanical fixation, inflection control, and skin compatibility. The distal end of the catheter is commonly contained within the bladder by inflated balloon, winged-shaped tip configurations which expand within the bladder, or pre-shaped curved catheter tips which curl to their original J-shape when stiffening wire is removed from the catheter lumen.

A problem with this form of distal end emplacement through the bladder wall is that it is only unidirectional; that is, it only resists the inadvertent pulling out of the tip of the catheter from the wall of the bladder, while allowing the catheter to freely pass further into the bladder, and back out up to the point of the containment structure. This continuing catheter motion in and out of the bladder puncture site may irritate tissue and cause infection or other difficulty at the bladder-catheter interface. Urine is especially irritating to most parts of the human body that are outside the urinary tract.

Dilators

Dilation is accomplished by pushing successively larger urethral dilation tubes through the urethra to increase the size of the lumen, a procedure which is painful and traumatic to the patient. Surgical treatment of strictures involves surgical risks as well as complications, including infection, bleeding and restenosis, which requires further treatment.

With the exception of balloon catheters, the current art of dilators has also changed little over the passage of time. A shaft with an increasing taper, bulbous structure, or enlarged end is pushed from without the passage to advance the tool through the restricted passage, thus forcing by longitudinally-applied pressure the lateral expansion of the passage walls. This push-to-advance method necessitates a stiff shaft which has all the same liabilities as traditional catheters. Catheters inherently provide a degree of this dilatorial function to the extent that the passage is opened sufficiently to accommodate the catheter.

Occluders

Occluders are used in some cases to control incontinence. Occluders of the prior art are constructed and applied with the same push-to-advance concept as catheters and dilators described above, with the same liabilities. The basic occluder is a bulb or plug on a shaft which is inserted within a passageway to stop or prevent the normal flow of materials through the passageway, or driven all the way into the bladder, for example, and allowed to seat as a plug at the neck of the urethra to prevent the flow of urine from the bladder.

Stents

A stent is a tubular metallic mesh device that is implanted to open and support a stricture to allow for urine flow. The stent body is between 3.5 cm and 6.5 cm in length depending on the anatomy, and is expandable by design to anchor in place. The stent being a mesh has openings that allow the tissue to grow through the wall making removal difficult and causing encrustation that reduces urine flow.

Intraurethral Valved Catheters

An intraurethral valved catheter is a device that is implanted to control the flow of urine with an integral valve that is remotely actuated. Since the entire catheter length is within the urethra, the chance for external infection is reduced. The anchoring mechanism of current designs is accomplished with balloons, or "petal like" projections from the catheter. Both designs are complicated to install and difficult to remove, and if the valve fails, leaves the patient in a painful and dangerous situation.

Patents in the Prior Art

There has been patent activity in the prior art indicating dissatisfaction with the push-to-advance methodology. Catheters have been adorned with a wide assortment of spiral and threaded features described as intended to ease the trauma and pain of what clearly remained a push-in device. Alvord's U.S. Pat. No. 207,932 (US), Peyret's 564,832 (French), Hayes' U.S. Pat. No. 1,644,919 (US), and Jacoby's U.S. Pat. No. 1,888,349 (US) are representative of these. In all cases, these disclosures fail to recognize that the basic push technique is fundamentally flawed and should be abandoned, and fail to resolve the critical features of structure necessary for rotational advancement as a substitute for the push method.

Other art reveals the use of spiral features for different purposes. For example, Spinosa's U.S. Pat. No. 3,815,608 (US), discloses a catheter with a thread designed to hold the urethral wall away from the shaft to allow urine to flow around the outside of the catheter. These disclosures likewise reveal a reliance on push-in methods or an assumption that such structures can be pulled out without regard to the spiral features, again failing to recognize rotation as a viable substitute for push, and failing to resolve the critical features of structure necessary for effective rotational advancement.

As a further indication of the failure of prior art similar to the above inventions to provide effective improvements to push-in methods, there is no apparent indication among the products commercially available, or in the medical practices known to the applicant, that any of these spirally ornamented devices were ever found to be viable.

Gastrointestinal Endoscores

The current device used for inspection and treatment of the GI (gastrointestinal) tract is a flexible Endoscope. This device takes a high level of skill to use, is difficult to maneuver and can be very painful for the patient, due to the basic push-to-advance design that has not changed since the device was invented in the early 1960s. The distal tip of the endoscope has the following parts:

1. a channel opening for suction and passage of accessories,
2. the light guide lens to distribute light from the fiberoptic bundle to illuminate the visual field,
3. the objective lens to focus an image of the mucosa onto the face of the image bundle and transmit it back to the eye piece,
4. an air/water jet, which supplies air to inflate the organ being observed, and water to clean off the image lens.

The Bending Section is the distal end of the tube, ranging from approx. 8–15 cm long, which can articulate to steer the scope as it is pushed inward and is controlled by a cable mechanism that is connected to control knobs on the proximal handle.

The Insertion Tube, which makes up the rest of the 60–150 cm length, is not capable of controlled deflection. It has a tailored bending flexibility and torque transmission which is of major importance in endoscope design. Most instruments have two-stage bending stiffness, i.e., the distal portion of the insertion tube is more flexible than the proximal portion. The Flexibility of each portion of the insertion tube requires extensive clinical testing to ensure that the endoscope handles easily and produces a minimum of patient discomfort.

The colon is a tubular organ which runs from the cecum in the right lower quadrant to the rectum. It is widest in the cecum and ascending colon and gradually narrows as one approaches the rectum. The colon is divided into the following sections:

a. the cecum; the ascending colon, which runs cephalad (towards the head) from the cecum to the hepatic flexure;
b. the transverse colon, which runs from the hepatic flexure in the upper quadrant of the splenic flexure in the left upper quadrant;
c. the descending colon, which runs caudad(toward the feet) from the splenic flexure to the left lower quadrant;
d. the sigmoid colon, which runs from the left lower quadrant to the rectosigmoid junction; and
e. the rectum, which extends down to the anal canal.

The inner layer of circular muscle is present throughout the colon. The outer longitudinal muscle in the wall of the colon is fused into three bands, the teniae coli. These bands start at the base of the appendix and run in the wall of the colon down to the rectum where they diffuse into the muscular coat. The three teniae cause the colon to have a triangular appearance endoscopically; this is especially prominent in the ascending and transverse colon. The haustra are outpouchings of the colon, separated by folds. In the descending colon the endoscopic appearance is often tubular.

Most experienced colonoscopists use similar endoscopic techniques. Air is introduced to inflate the colon, but as little as possible to prevent overdistension. The pressure on the device is gentle to avoid stretching the colonic wall or mesentery (the connective tissue that holds the colon like a fan) which can cause pain, a vagal episode, or a perforation. The lumen is kept in view at all times; little or none of the examination is performed blindly, because you are pushing a stiff instrument.

A variety of in and out maneuvers are used to "accordian" the colon on the colonoscope, keeping the colonoscope free of loops as possible. In the difficult colon, special maneuvers such as the creating of an alpha loop in the sigmoid colon are used to pass the sharply angulated sigmoid/descending colon junction. This maneuver may require fluoroscopic guidance and training in the technique.

The colonoscope is advanced to the cecum under direct vision. The detailed examination of the mucosa is usually performed as the colonoscope is slowly removed from the cecum.

To inspect the whole length of the large intestine requires a highly skilled practitioner, which makes the procedure costly. Even still the procedure can be very painful for the patient, making sedation necessary. This is due to the inherent deficiencies in the "push-to-advance" design.

In summary, there are problems in making present push-in catheters, dilators, and occluders stiff enough for penetration and flexible enough to make the turns without undue risk of trauma to the wall of the passageway when being pushed in; and once installed, comfortable enough to wear for an extended period. The problems with stent encrustation and removal are well known. Self-administration is inhibited by all of the short-comings of the prior art. Further injury, infection and discomfort can result from unskilled or improper technique. The problems with colonoscopy have been previously described.

The long history of push-in catheters/dilators and occluders has gradually crystallized into an industry wide, self-perpetuating, fundamental assumption that catheters are to be mainly pushed through bodily passageways, albeit with some rotational easing. This "fact" is so widely perpetuated and pervasive in the commercially available products and medical practices as to have stifled original thinking in this art. This, in spite of it's well-recorded short comings of pain, trauma, risk of rupture, and failed, aborted or incomplete procedures and need for skilled practitioners and special equipment for monitoring and safeguarding against the inherent problems.

SUMMARY OF THE INVENTION

For the purposes of this disclosure, including the appended claims, the terms "distal", "distally", and "distal end", as they relate to the devices and methods described herein, refer to the end of the device further from or in the direction away from a practitioner who might be applying the device or method to the subject. Stated otherwise, the terms refer to the end of the device closer to or in the direction towards the subject's interior.

The terms "proximal", "proximally", and "proximal end", as they relate to the devices and methods described herein, refer to the end of the device closer to or in the direction towards the practitioner who might be applying the device or method, rather than the subject.

Objects of the invention include providing and employing screw-based means for rotational advancement and anchoring of catheters, probes, occluders, stents, and dilators into genitourinary and gastrointestinal passageways such as the urethra, ureter, esophagus and fallopian tube, and for the emplacement of suprapubic catheters for draining genitourinary organs such as the bladder, whereby the subject device is applied through a natural body orifice or surgically created opening and is drawn through the passage by the longitudinal pull of a helix on the walls of the passage or organ as the device is rotated. This technology is a radical departure from the 4000 year old traditional "push to advance" methodology previously discussed.

Indwelling and Intermittent Catheters

Flexible, thin wall indwelling and intermittent catheters and related devices and delivery stylets, made possible by this form of emplacement, are less traumatic and easier for the medical practitioner or patient to use. The catheter of the invention eliminates the problems of conventional devices by using helix or rotational technology that provides controlled insertion and flexibility to negotiate the urethra. The helix design accomplishes a pre-dilatation of the passageway at a steady rate that relaxes the sphincter and lessens or prevents spasm. Once placed, the device is anchored by the radial displacement and close pitch of the helix, preventing longitudinal migration due to body movement or fluid flow.

In another embodiment, the helix is located on the shaft under a Foley-type balloon and disappears when the balloon is inflated. The flexible reinforced shaft need be only about half the wall thickness of conventional Foley Catheters, which means a smaller OD catheter can be used. The helix advances the shaft and dilates the urethra as the catheter is inserted. Once the bladder is reached the balloon is inflated with sterile water, the helix is engulfed by the balloon. The process is then reversed to remove the catheter. This technology fosters reduced costs for patent care, improved clinical outcomes and enhanced patient quality of life.

Continence Catheter with Valve

The continence catheter of the invention, indicated for bladder outlet obstructions, is intended for BPH patients who are not able to, or choose not to undergo TURP. This embodiment of the invention allows the urethra in the area of the prostate to remain open. At the proximal (external end) of this catheter there may be a flow valve which can be depressed or otherwise opened to empty the bladder. The catheter may be produced as a sterile, single-use, disposable item that can be used once and replaced as needed.

The same embodiment of the catheter of the invention provides a female Stress UI sufferer with lifestyle benefits that greatly outperform absorbent products intended to manage this condition.

The patient simply inserts the catheter into the urethral opening and rotates the shaft to advance the catheter into the bladder. This can be done in the morning in the convenience of home. When the user needs to urinate, the valve end of the flexible shaft may be exposed through the clothing and the valve opened to empty the bladder. Since the device is not removed and reinserted after each voiding the risk of infection is reduced. At the end of the day the catheter is easily removed and disposed.

Intraurethral Valved Catheter

The male or female intraurethral valved catheter of the invention is indicated for bladder control. This embodiment of the invention allows the flow of urine to be controlled by a valve mechanism that is within the catheter. This valve may be actuated directly by insertion of a tool such as a stylet, or remotely by using a magnetic field device.

The intraurethral device reduces the potential for infection by eliminating the external tubing which can be an entry path for bacterial contamination. These catheters are typically 3.5 to 6.5 centimeters in length, depending on the anatomy, and have the helical element of the invention on the outer diameter of the body. The thread height of the helix may vary over it's length, as an aid to the advancement and retention characteristics of the device. The sidewall of the catheter may be reinforced to resist collapsing due to contraction pressure. This catheter may be inserted in the urethra under fluoroscopy, using a detachable flexible stylet which keys into the proximal end of the catheter in a non-rotational fitment, and may be inserted in an outpatient procedure using topical anesthesia.

Stents

The stent of the invention, indicated for bladder outlet obstructions, keeps the urethra open in the area of the stricture. The stent body may be between 3.5 cm and 6.5 cm in length depending on the anatomy, and has a helical element on the outer diameter of the body to advance and retain the stent. The sidewall of the stent may have a reinforcement means to prevent collapsing due to prostate pressure. The stent can be inserted in the urethra under fluoroscopy, using a detachable flexible stylet which keys into the proximal end of the stent body, and may be inserted in an outpatient procedure using topical anesthesia.

The stents of the invention are not susceptible to being incorporated by the urethral mucosa in a manner preventing rotation, thereby permitting a lengthy period of emplacement and subsequent removal by the same rotational technique. The stent may also have a sufficiently large internal diameter, or lumen, to permit cystoscopies, thereby allowing examination of the bladder without removing the stent.

Dilators and Occluders

Helically-adapted dilators and occluders of the invention are likewise rotatingly advanced and retracted; the helical element performing a dilatory function to some degree. Dilators of respectively larger diameters may be used to achieve a gradually more pronounced effect The rotational advancement means may be combined with the push-to-advance methodology in any of these devices. In a dilator, for example, a helically equipped leader shaft extending distally of the bulbous portion of the device rotatingly advances the device up to the point that the helix passes out of the interior end of the passage, the remainder of the leader shaft then providing a guide wire that leads the bulb through the remainder of the passageway when the dilator is pushed from the proximal end.

Suprapubic Catheters

The adaptation of the invention to suprapubic catheters used in a classic transabdominal puncture for the drainage of the bladder or other genitourinary organs, permits the helix on the distal end of the catheter to be emplaced in the wall of the organ far enough so that the helical vane extends from both sides of the organ wall, so that the longitudinal sliding motion of the catheter into and out of the organ is inhibited by the helical vane. This reduces a source of irritation and associated complications at the organ wall entry point.

The helically-adapted suprapubic catheter may be placed in the organ using ultrasound or fluoroscopy to visualize placement, by rotatingly advancing the catheter over a guidewire leading to the organ; the guidewire having been installed through a tubular access created by using a cannula and trocar to reach the organ, the trocar and the cannula having been successively removed.

General Construction

Any embodiment of the invention may be radiopaque, or have radiopaque features, markers or other components, permitting the use of fluoroscopy to monitor emplacement or removal of the device, or even the rotational orientation and rotational movement.

The thread element may be solid, hollow, or fluid filled. It may taper in height at various locations to optimize advancement and anchoring. Embodiments or elements of the invention may be fabricated, molded, wound, extruded or otherwise constructed of non-toxic, non-corrosive materials or combinations of materials that are otherwise tolerant of bodily fluids and durable when implanted in vivo. Such materials may include but are not limited to polyurethane, medical grade stainless steel, silicone, bicarbon, polytetrafluoroethylene, tantalum, titanium, or nickel-titanium alloy. Conversely, materials may be specifically chosen to be bioabsorable so as to obviate the need for removal.

The devices of the invention may be enhanced with one or a combination of the following coatings: water based hydrophilic, antibacterial coatings such as nitrofurazone, bateriostatic coatings such as silver, or other mediations to further enhance their clinical performance.

Camera Introducer

The threaded camera introducer system, briefly stated, presents a novel means for the introduction of sensors and other implements into and through the fall length of the colon. The fundamental structure of the introducer, consistent with the rotate-to-advance structure and methodology of the invention, is a large, soft, flexible worm-like tubular device with a helix of soft, pliant threads which translate rotational force at the proximal end to a pulling action on the colon wall.

The hollow core or central lumen connects the distal and proximal ends of the tube. A camera head or other visual sensor can be introduced into the device and arranged to "see" forward from the center of the bulbous tip on the distal end. Light bundles or wires connected to the camera pass through the central lumen and out the proximal end of the device to an appropriate control and viewing apparatus.

The distal end of the device is gently urged into the rectum sufficiently far to engage the helix. The device is rotated from just outside the point of entry, to slowly advance into and through the entire length of the colon to the cecum. The helical threads pulling the device gently along the interior colon wall; the flexibility of the device allowing it to easily negotiate the major turns of the colon. The larger threads at the distal end provide the greatest grip or pull, the smaller threads closer to the proximal end contributing a lesser degree of grip or pull. The device is removed using the same method in reverse.

As illustrated in the figures, the light bundles or cables may be encased in a flexible torque tube or assembly which provides or contributes to the torsional strength necessary to rotatingly advance and withdrawn the device.

The interior wall of the main tubular device or introducer, may be configured to contain the torque tube or vertebra in a non-rotational manner, such that torque applied at any place on the exterior wall of the introducer is transmitted to the torque tube and hence over the full length of the device.

Various embodiments and enhancements are possible, all within the scope of the invention:

1. The helical thread or spiral extending the length of the device may be used for auxiliary purposes, including to:
   a) Carry fluids into the colon/passage,
   b) Provide vacuum to the passage way itself or vacuum within the device to facilitate the advancement of the camera or endoscope into the device, c) Convey light bundles or electrical wires for specific purposes, and/or d) Provide depth markers to assist the practitioner in determining the general position of the device within the body.

2. The spiral may also be inflated with a fluid during entry to obtain fall thread form and rotationally grip or fix the catheter to the camera element, and deflated to permit non-rotational removal by pulling the device through the colon.

3. The video screen or the image on the screen as seen through the rotating camera introducer as it advances, may be electronically processed to hold the image in a non-rotating, stationary manner for the benefit of the person administering the procedure.

4. The distal portion of the device may be relatively more flexible to enhance trackability along the path of the colon/passageway.

5. The device may have sufficient torque transmission capability from the proximal to the distal end so the distal portion of the device can be thus rotated at full length in the colon without interior support.

6. The distal tip or zone may have a sufficient thread height to grip the colon wall and provide the primary "pulling power" to advance the device into the body and negotiate the turns, while the somewhat lower thread height along the balance of the device is adequate to support rotational advancement without drag and avoid bunching or gathering the colon wall.

7. There are at least three methods of containing and controlling this 160 cm long instrument to ensure it remains within the operating field:

a) A dispensing device as shown in FIG. 34, b) A straight tubular component, or c) Held by an assistant.

8. Material of construction:

a) The main body may be produced from polyvinylchloride plastic and may be reinforced with wire or fabric.

b) The helix may be made of PVC and may be reinforced with wire or otherwise.

c) A distal end window may be a flat, optically clear plastic lens made from PVC, polycarbonate, or acrylic plastic.

9. Alternative Uses:

a) Variations on the introducer device within the scope of the invention include full length tubes, or short sections analogous to urethral stents, being emplaced in the colon by the rotational structures and techniques of the invention for temporary purposes such as to aid in the repair of a damaged colon or a related abdominal injury or condition, by providing a supplemental lining and/or form to the colon or to a section of the colon.

10. Camera with torque control umbilicus:

a) The camera body which houses both the camera and the light sources may be made of stainless steel or molded with a dimensionally stable plastic such as polycarbonate.

b) The vertebrae which makes up the torque control umbilicus may be made of a high strength thermoplastic or a metal such as stainless steel or beryllium copper.

By means of the invention, the entire colon can be examined without the need for a conventional colonoscope or endoscope, and without the attendant expertise, pain, medication, post procedure recovery time, and cost. The means and method of the invention require less training and have far greater likelihood of reaching the cecum, (far end of the colon), than conventional tools and procedures. Other body cavities and passageways may be similarly examined. The camera introducer catheter can be used in four different modes:

1. As an INTRODUCER, it includes the following characteristics and benefits:

a) Conveys a camera assembly along the entire colon to screen patients for polyps, lesions, cancer sights and other maladies.

b) The entire colon can be examined without the need for a conventional colonoscope/endoscope.

c) A total examination of the colon can be successfully performed with significantly less manipulation technique, pain, medication and post procedure recovery time.

d) Requires less training and has greater success in reaching the cecum.

e) As a single-use disposable device, allowing the expensive camera with its torque controlled umbilicus to be used repeatedly without danger of sequential infections.

f) Procedure is less expensive when compared to the cost of cleaning and repairing the conventional endoscopes and amortizing the cost of today's costly video processing unit.

g) The procedure can be successfully performed by less specialized, less expensive individuals.

h) The INTRODUCER is supplied sterilized and ready for use.

2. As a more CONVENTIONAL STYLE ENDOSCOPE:

By adapting a conventional endoscope to the structure and method of the invention, the benefits of the invention are coupled with the following conventional functions:

a) Tip articulation.

b) Air & water delivery.

c) Suction of fluids.

d) Illumination of passages.

e) Imaging capability.

f) Drug delivery.

g) Accessories.

3. As a HYBRID CATHETER having some of the functions and features of the more CONVENTIONAL ENDOSCOPE and/or the INTRODUCER style built into the device for procedure-specific applications. Also, it could be used in conjunction with or independent of conventional endoscopic devices and accessories.

4. As a TRANSPORTER or introducer to deliver a conventional endoscope to any location of the colon or other passageway. This may occur by:

a) Providing a fluid tight envelope for the endoscope.

b) Providing a means for the endoscope to exit the distal end of the INTRODUCER to perform diagnostic/therapeutic procedures normally done with the endoscope.

Still other objects and advantages of the present invention will become readily apparent to those skilled in this art from the following detailed description, wherein I have shown and described preferred and other embodiments of the invention, simply by way of illustration of the best mode contemplated by me on carrying out my invention. As will be realized, the invention is capable of other and different embodiments, and its several details are capable of modifications in various obvious respects, all without departing from the invention.

BRIEF DESCRIPTION OF THE DRAWINGS

FIG. 2 is a perspective view of a threaded catheter for a male.

FIG. 3 is a cross sectional view of the threaded portion of the catheter of FIG. 2.

FIG. 4 is a illustration of the threaded end of the catheter of FIG. 1 engaged in the urethra.

FIG. 5 is a perspective view of a threaded catheter for a female.

FIG. 6 is a cross sectional view of the threaded portion of the catheter of FIG. 5.

FIG. 7 is a perspective view of a threaded catheter and flexible shaft stylet with which it is installed.

FIG. 19 is a perspective view of a stylet with a grip on it's proximal end and a hexagon drive tip on it's distal end.

FIG. 20 is a perspective view of the hexagon drive tip of the stylet of FIG. 19.

FIG. 21 is a perspective view of a stent-follower with a helical element at it's distal end.

FIG. 22 is a cross section closeup view of the distal end of the stent-follower of FIG. 21, showing the hidden portion of the bushing with it's hexagonal drive aperture in dashed lines.

DESCRIPTION OF THE PREFERRED EMBODIMENT

To those skilled in the art, the invention admits of many variations and appellations in apparatus and methodology. By way of example, there is provided in accordance with the present invention, a rotate-to-advance structure and methodology applicable to a range of medical devices that have here-to-fore relied entirely or substantially on a push-to-advance technique for penetration of bodily passages. Such devices include catheters, dilators, and occluders for mammalian genitourinary or gastrointestinal passages such as the urethra or ureter for the usual purposes associated with such devices where no incising or rupture of passage walls or membranes is intended.

Catheters

Figure 1:
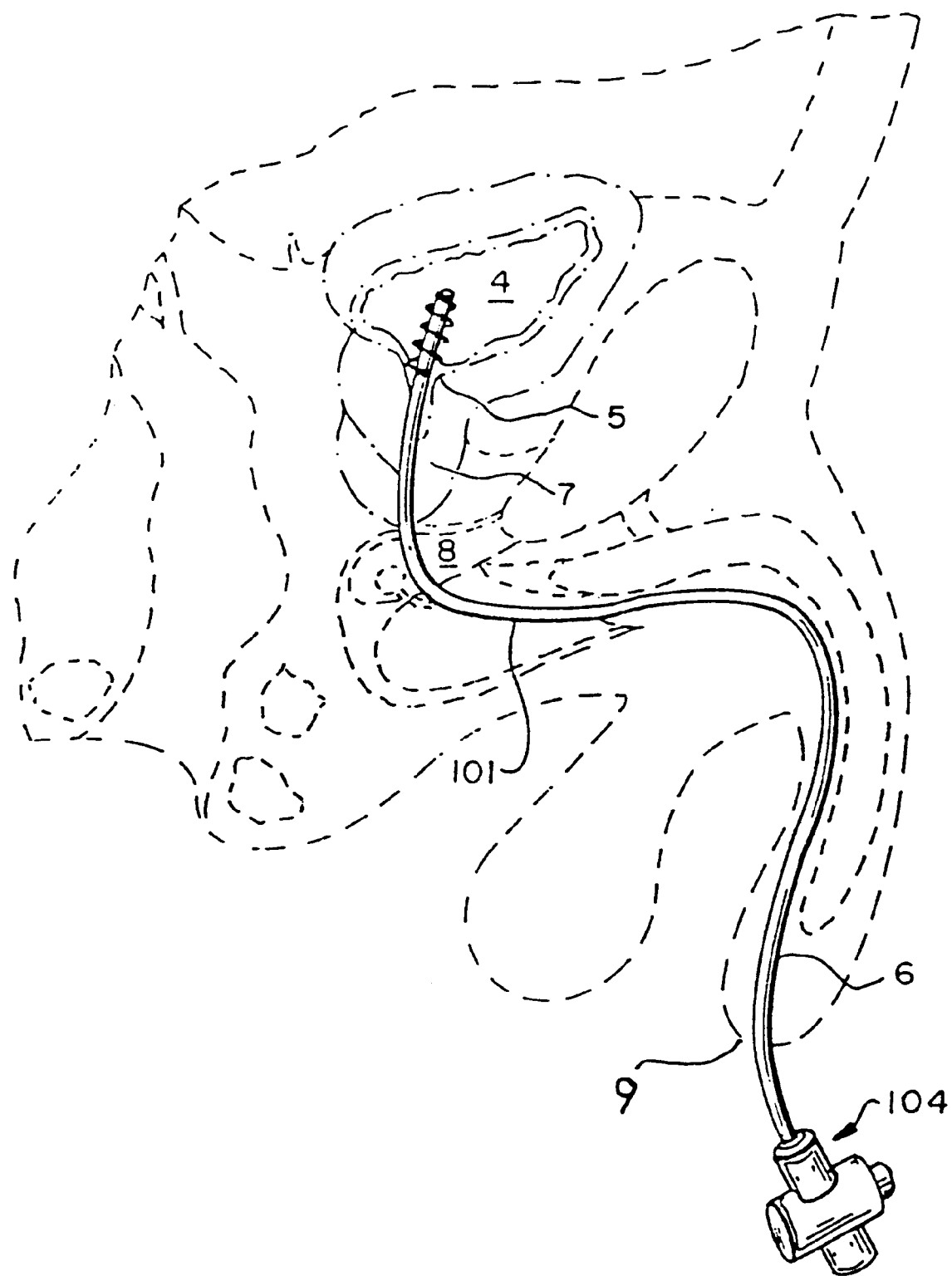
FIG. 1 is an illustration of the lower abdominal anatomy of a male subject, with the threaded portion of the catheter of FIG. 2 extending into the bladder.

Referring now to FIGS. 1, 2 and 3, threaded catheter 101 for males is made up of tube 102 with external thread 103, attachable to flow control device 104. Tube 102 is extruded from polyurethane material, has an inside diameter of 0.06 inches, an outside diameter 103d of 0.125 inches, and is approximately 13 inches long. The durometer as measured on the smooth, outside wall of the tube is 85 Shore A. Distal end 105 is closed off, with it's tip rounded to a uniform radius of about 0.06 inches. Proximal end 106 of tube 102 is simply cut off square and attached to flow control device 104. Tube 102 is sufficiently strong such that when the majority of its length is contained within the urethra, it will withstand and transmit torque as applied by finger force at the lower end external of the urethra, to the thread.

A useful alternative embodiment of catheter 101 incorporates the recited external thread 103 for rotational advancement, but provides for the central lumen to connect to or terminate in a straight-through or axially aligned drainage port at the distal tip of the catheter, similar to the most basic conventional catheters. This is likewise useful for drainage and also enables the insertion or passage of guide wires or other devices where specific procedures require it.

Referring to FIGS. 2 and 3, external thread 103 is formed from a strip of polyurethane material with a rectangular cross section of width 103a, 0.05 inches, and height 103b, 0.032 inches, and continuously attached over it's length to tube 102 starting 0.2 inches from distal end 105 and extending four complete turns around tube 102 in a clockwise direction towards proximal end 106 at a uniform pitch 103c of 0.25 inches, resulting in a four-turn thread or helix about one inch long.

It is readily apparent from the dimensions of FIGS. 2 and 3 that the thread height 103b of catheter 101 is greater than twenty percent (20%) of the 103d thread diameter. This relative height is necessary to expand and penetrate the longitudinal folds of the urethra to a sufficient depth to achieve a useful grip by the thread.

The diameter of the helix formed by thread 103 of catheter 101 is referred to as thread diameter 103d, and is equal to two thread heights 103b plus the outside diameter 102d of catheter tube 102, or in this case 2 times 0.032 inches plus 0.125 inches or approximately 0.19 inches. The circumference C of the helix formed by thread 30 is calculated as $\pi$ (pi) times thread diameter 103d, or in this case 3.14 times 0.19 or approximately 0.6 inches.

$$C = \pi \cdot 103d$$

The ratio R of thread pitch 103c, 0.25 inches, to the circumference of thread diameter 103d, at 0.6 inches, is much less than 1 to 1, thereby improving the leverage of the screw thread for converting rotation into longitudinal pulling power as compared to ratios larger than 1/1.

$$R = 103c/C$$

The shoulders of thread 103 have a radius of 0.015 inches. In small quantities, thread 103 may be attached to tube 102 by wicking tetrahydrofuran (THF) solvent under the thread using a fine hollow tube. Catheter 101 may be molded in large quantities with thread 103 being an integral part of the molded structure.

Referring to FIG. 4, two drainage ports 107, connecting to lumen 108, are oval in shape, the major axis of the oval being parallel with the axis of tube 102 and about 1.5 times the minor axis, which is about equal to the diameter of the lumen. The two ports are configured 180 degrees apart radially, and spaced longitudinally to fit between the turns of thread 103.

Both ends of thread 103 are tapered from zero to full height in one-half turn of the helix, to facilitate gentle, gradual displacement of urethra wall 002 by thread 103 when catheter 101 is rotated clockwise for advancement into the urethra and counterclockwise for retraction. The difference between thread width 103b and pitch 103c shown in FIG. 3 is sufficient that the urethra wall 002 does not bridge between adjacent turns of thread 103, but rather is only displaced in a manner closely conforming to the cross section of thread 103, thereby providing the longitudinal grip on urethra wall 002 for advancing and retracting the catheter.

Referring to FIG. 1, catheter 101 is shown in proper position for draining bladder 004, after it has been advanced through the urethra 006 until the helix passes out of the urethra into the bladder.

It is apparent from the anatomy shown in FIG. 1, that thread 103 must be limited in length to be advanced to any point above the sphincter 008, so that the sphincter may contract directly onto the smooth, round, exterior of tube 102, thereby preventing leakage around the tube, and further constraining catheter 101 from migrating or being forced out of the urethra by pressure from urine in the bladder. It is further apparent from the figure that there is a limit to the length of thread 103 on a catheter that can be advanced to a position above the sphincter 008, not more than about six turns within the optimal range of thread pitch, and still fit within the bladder 004 without interference. A limited length of thread 103 also localizes the area of pulling force to the upper end of catheter 101, assuring that the trailing length of the catheter is drawn, not pushed, through the passage.

Referring to FIGS. 5 and 6, threaded catheter 111 for females, similar to catheter 101 for males, is made up of tube 112 with thread 113, attachable to flow control device 114. Tube 112 is extruded from polyurethane material, has an inside diameter of 0.063 inches, an outside diameter 112d of 0.125 inches, and is approximately seven inches long. The durometer as measured on the smooth, outside wall of the tube is 85 shore a. Distal end 115 is closed off, it's tip rounded to a uniform radius of about 0.06 inches. Proximal end 16 of tube 112 is simply cut off square and attached to flow control device 114. Tube 112 is sufficiently strong such that when the majority of its length is contained within the urethra, it will withstand and transmit torque as applied by finger force at the lower end external of the urethra, to the thread or helix.

Referring to FIGS. 5 and 6, thread 113 of catheter 111 is formed from a strip of polyurethane material with a rectangular cross section of width 113a of 0.05 inches and height 31b of 0.10 inches, attached to tube 112 starting 0.2 inches from distal end 115 and extending four turns around tube 112 in a clockwise direction towards proximal end 116 at a uniform pitch 113c of 0.25 inches, resulting in a four-turn thread or helix about one inch long.

It is readily apparent from FIGS. 5 and 6 that the thread height 113b of catheter 111 at 0.10 inches, is much greater than twenty percent (20%) of tube diameter 112d, at 0.125 inches. This relative thread height is necessary in order to expand and penetrate the longitudinal folds of the female urethra sufficiently far to achieve a useful grip by the thread.

Similar to the description of threaded catheter 101, the diameter 113d of the helix formed by thread 113 is equal to two thread heights 113b plus the diameter 112d, or in this case 2 times 0.10 plus 0.125 or approximately 0.33 inches. The circumference C of the helix formed by thread 113 is calculated as $\pi$ (pi) times the thread diameter 113d, or in this case 3.14 times 0.33 or approximately 1.0 inches. The ratio R of thread pitch 113c, at 0.25 inches, to the circumference C, at 1.0 inches, is again much less than 1 to 1, thereby improving the leverage of the thread for converting rotation into longitudinal pulling power as compared to larger ratios.

The shoulders of thread 113 have a radius of 0.015 inches. Catheter 111 may be constructed or fabricated by the same means as catheter 101.

Referring to FIG. 5, two side drainage ports 117, connecting to lumen 118, are oval in shape, the major axis of the oval being parallel with the axis of tube 112 and about 1.5 times the minor axis, which is about equal to the diameter of the lumen. The two sideports 117 are configured 180 degrees apart radially, and spaced longitudinally to fit between the turns of the thread.

Referring to FIG. 5 and 6, the ends of thread 113 are tapered from zero to full height in three-quarters turn of the helix, to facilitate gentle, gradual displacement of urethra wall by the thread when catheter is rotated clockwise for advancement and counterclockwise for retraction. The difference between width 113a and pitch 113c is sufficient that the urethra wall does not bridge between adjacent turns, but rather is displaced in a manner closely conforming to the profile of the thread, thereby providing the longitudinal grip on the urethra wall for advancing and retracting the catheter, the same as catheter 101 of FIGS. 2 and 3.

The optimal position for threaded catheter 111 for draining the bladder of a female subject is where it is advanced through the urethra until the thread passes out of the urethra into the bladder, similar to how catheter 101 is illustrated in FIG. 1, but for females.

A detailed method of self-administration of the urethra with the appropriate respective threaded catheter 101 or 111, or other similar threaded devices, is explained: The user assembles materials including a sterile threaded catheter 101 or 111, a container for urine, soap and water, if the catheter is not pre-lubricated then a water soluble lubricant, a mirror (for females), and tissues. The user will then wash the hands and urethral opening with soap and water, squeeze out a small amount of lubricant into clean tissue, dip the distal end tip of the catheter into the lubricant, and manually engage the tip of the catheter into the urethral opening, (the mirror may be helpful for females to assist in locating the opening).

The user will then gently push and turn the catheter in far enough to engage the thread about one full turn with the urethra, and gently rotate the tube of the catheter in the direction of the thread, preferably clockwise, to advance the catheter into the urethra until urine appears in the tube. The user then pauses to drain the bladder, directing the urine into the container, then resumes rotation of the catheter until it is no longer advanced by the rotation, indicating that the thread of the catheter has passed into the bladder and the catheter is in proper position.

The user then places a flow control device on the proximal end of the catheter and empties the bladder periodically as required. The catheter is removed when appropriate using similar precautions for cleanliness and containment, by rotating the catheter in a direction opposite the direction of insertion, presumably counterclockwise.

Figure 8:
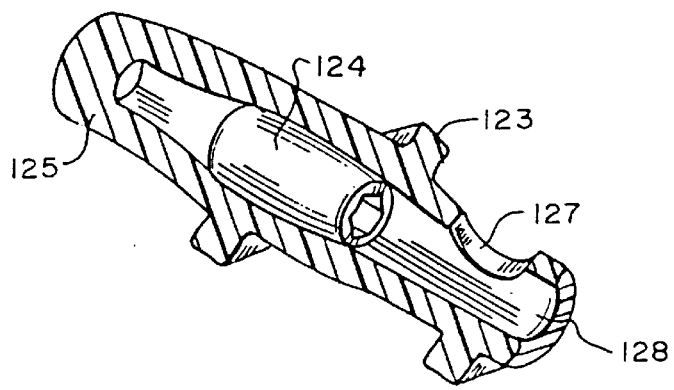
FIG. 8 is a cross section of the tip of the catheter of FIG. 7, showing the non-rotational fitment that receives the tip of the stylet of FIG. 7.
Figure 9:
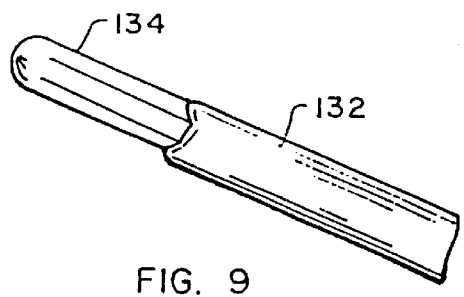
FIG. 9 is a perspective view of the tip of the stylet of FIG. 7 that is insertable into the fitment of FIG. 8.

Referring to FIGS. 7, 8 and 9, another embodiment contemplated by the claims is illustrated by catheter 121, which is made up of tube 122 with thread 123 applied in the form of a helix, and utilizing flexible shaft stylet 131 as an insertion and retraction tool. Stylet 131 has grip 133 at the proximal end, for turning. Tube 122 is configured with non-rotational fitment 124 near distal end 125 so that stylet 131 can be inserted through proximal end 126, up through lumen 128 of tube 122, and tip 134 of stylet 131 be then engaged with fitment 124 in a manner that allows rotation of grip 133 in one direction to rotate catheter 121 for advancement into the urethra, and in the other direction for retraction.

The flexible shaft 132 of stylet 131 is sufficiently strong such that when it is fully inserted into catheter 121, it will withstand and transmit torque as applied by finger force at the proximal end knurled knob grip 133 external of the urethra, to the thread 123. Stylet 131 is removed after catheter 121 is installed, and reinserted for retracting the catheter when required.

Fitment 124 is an elongated collar with a multi-faceted interior wall, securely anchored within tube 122, and configured to receive in a non-rotational relationship tip 134. Tip 134 is configured with a corresponding elongated, multi-faceted exterior shape and rounded end, to readily enter fitment 124. Stylet tip 134 and fitment 124 can be alternatively configured and connected by various means to provide a non-sliding as well as non-rotational connection.

Figure 11:
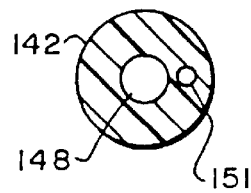
FIG. 11 is a cross section view of the shaft of the catheter of FIG. 10, showing the central drain lumen and the smaller inflation lumen.
Figure 10:
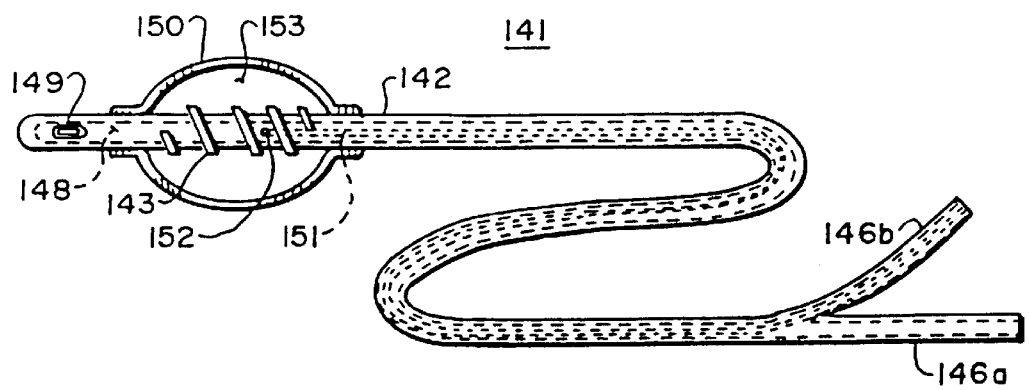
FIG. 10 is a diagrammatic longitudinal cross section view of a threaded balloon catheter showing the thread element inside the inflated balloon, with lumens shown as dashed lines.
Figure 12:
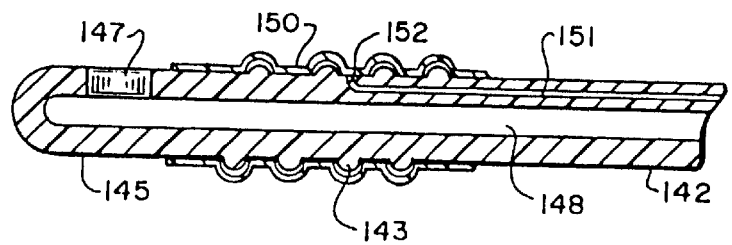
FIG. 12 is a longitudinal cross section view of the distal end of the catheter of FIG. 10, showing the balloon contracted around the helical element.

Referring to FIGS. 10, 11 and 12, a threaded foley-type catheter 141 of the invention is made from polyurethane material. It has a flexible tube 142 with an axial drainage lumen 148 running from a drainage port 149 to it's proximal end 146a, and a thread 143 applied to it's external surface near it's distal end 145 in the manner of threaded catheters previously described. Catheter 141 has a thin-walled inflatable elastic balloon 150 encasing the helical thread 143 and sealed to tube 142 above and below the thread 143. Drainage port 149 is located above or distally from balloon 150. A smaller inflation lumen 151 within tube 142 communicates between inflation port 152 within the envelope of balloon 150 to the distal end 146b of the catheter. Lumens 148 and 151 are isolated from each other, as indicated by FIGS. 11 and 12.

Balloon 150, when uninflated, is normally contracted tightly about helical element 143 as illustrated in FIG. 12, and may be inflated as in FIG. 10 by injecting fluid through lumen 151 into the balloon cavity 153. The flexible tube 142 is of sufficient torsional strength to withstand and transmit rotational finger force at the proximal end to thread 143.

Dilators and Occluders

Figure 13:
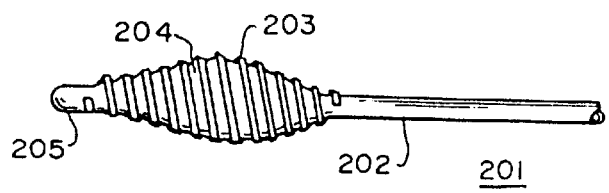
FIG. 13 is a side elevation of a threaded dilator.
Figure 14:
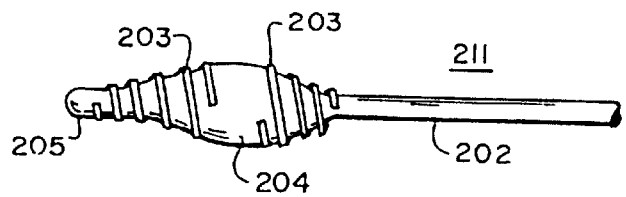
FIG. 14 is a side elevation of a threaded occluder.
Figure 15:
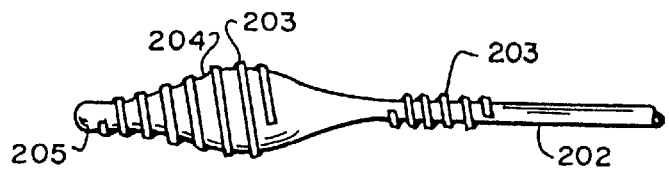
FIG. 15 is a side elevation of another variation of a threaded occluder.

Referring now to FIGS. 13, 14 and 15, dilator 201 and occluders 211 and 221 are similarly constructed by configuring the upper end 205 of a flexible shaft 202 with tapered bulb 204 near it's distal end, and disposing thereon one or two sections of thread 203. These threads are similar to thread 103 on catheter 101 of FIGS. 2 and 3, wherein the height of the thread is at least twenty percent (20%) of the diameter of the shaft 202, and the ratio of thread pitch to the circumference of the thread diameter at any given point on the bulb or shaft is less than one to one (1/1). The ends of threads 203 are tapered for ease of advancing and retracting, again similar to the threaded catheter of FIGS. 2 and 3.

Dilator 201, of FIG. 13, is configured with multiple turns of thread 203 extending over both ends of tapered bulb 204, and is used to dilate a constricted passage by being rotatingly advanced and retracted through the obstructed area of the passage in the same fashion as the threaded catheters of the invention.

Occluder 211, of FIG. 14, is configured with two sections of thread 203, leaving the midsection or bulbous portion of tapered bulb 204 smooth and round in order to provide a uniform occluding surface. This occluder is used to plug or constrict a passageway at an interior point; being rotatingly advanced to and retracted from that point in the same fashion as the threaded catheters of the invention.

Occluder 221, of FIG. 15, is configured with two sections of thread 203, the lower or proximal end thread 203 being disposed on the shaft 202 below the tapered bulb 204, leaving the lower tapered end of bulb 204 smooth and round in order to provide a uniform occluding surface. This occluder is used to plug a passageway at the interior end neck or entrance; being rotatingly advanced until the tapered bulb passes entirely through the passage while the lower thread remains engaged in the passage, and being then rotatingly retracted to seat the tapered bulb against the neck of the passage. The occluder is then rotatingly retracted when appropriate.

Stents and Intraurethral Valve Catheters

Figure 16:
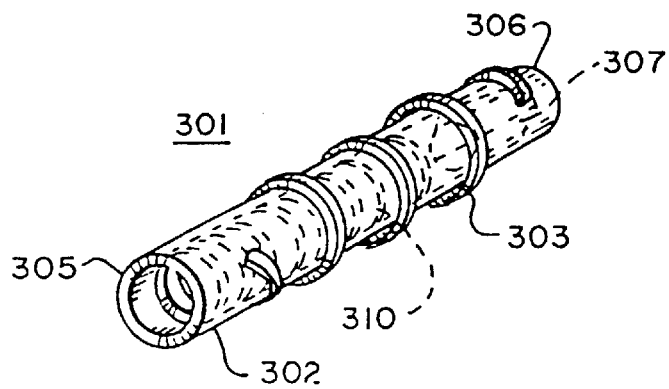
FIG. 16 is a perspective view of a threaded stent, dashed lines showing an internal sidewall reinforcement member and a bushing with a hexagon drive socket.
Figure 17:
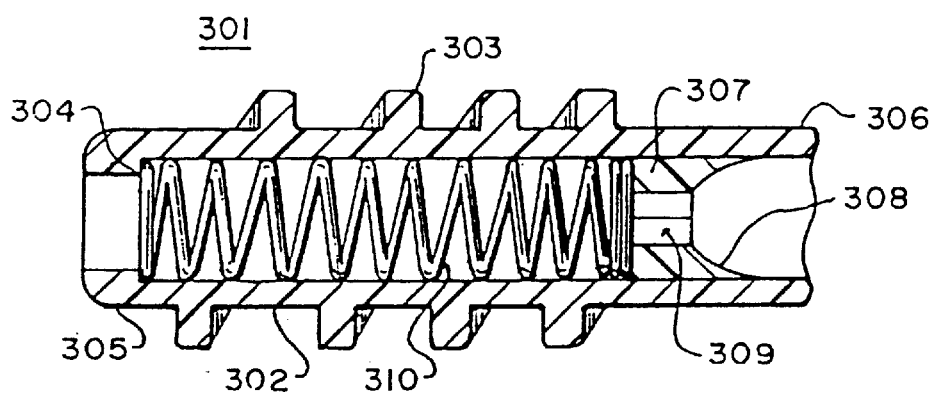
FIG. 17 is a cross section view of the stent of FIG. 16.
Figure 18:
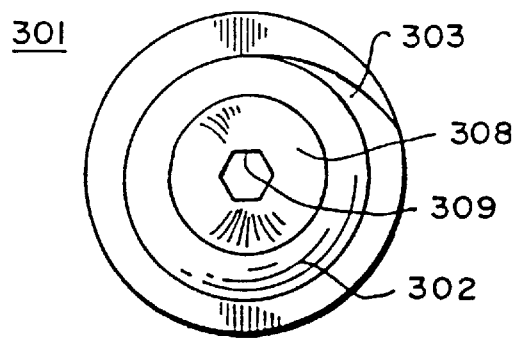
FIG. 18 is a proximal end view of the stent of FIG. 16, with the hexagon drive socket visible at the center.

Referring now to FIGS. 16–18, a threaded urethral stent 301 made from polyurethane material has a tube 302 with an external thread 303 of uniform pitch. Thread 303 is similar to thread 103 on catheter 101 of FIGS. 2 and 3, wherein the height of the thread is at least twenty percent (20%) of the diameter of the shaft 202, and the ratio of thread pitch to the circumference of the thread diameter is less than one to one (1/1). The ends of thread 303 are tapered for ease of advancing and retracting through a passage. There is an interior shoulder 304 at the distal end 305 of the stent, and a bushing 307 of relatively harder material with a tapered interior wall 308 extending from the bushing's full diameter at one end to a uniform hexagonal aperture 309, bushing 307 being affixed within the proximal end 306 of the stent and oriented with tapered wall 308 extending proximally from aperture 309. Coiled sidewall reinforcement member 310 is secured within the remaining length of stent 301 by bushing 307 and interior shoulder 304. Alternative embodiments may have a section of the thread being tapered to a lesser height or no height, to provide a "waist" for gripping by a muscular zone such as the prostate or sphincter. Also, reinforcement member 310 could be configured or molded into the sidewall tube 302.

Referring now to FIGS. 19 and 20, stylet 331, similar to stylet 131 of FIG. 7, has flexible shaft 332 with grip 333 at the proximal end for turning, and hardened hexagon tip 334 at the distal end which closely fits into aperture 309 of stent 301 in a non-rotational manner for emplacement of the stent by the method of the invention. The flexible shaft 332 of the stylet is sufficiently strong such that when tip 334 is inserted into aperture 309, the shaft will withstand and transmit torque as applied by rotational finger force at grip 333 to thread 303.

Referring now to FIGS. 21 and 22, threaded stent-follower 341 has a flexible tube 342, lumen 347 of which is sized to accept the ready insertion of tip 334 and shaft 332 of stylet 331 of FIG. 19. Tube 342 is of sufficient torsional strength to accept and transmit rotational finger force at it's proximal end 346 to it's distal end 345. A thread 343 of uniform pitch and not more than six turns is applied to the external surface of tube 342 near distal end 345. Thread 343 conforms to the same twenty percent (20%) rule of thread height to tube diameter, and ratio of thread pitch to thread circumference of less than one to one (1/1), as thread 103 in FIGS. 2 and 3 as described above. The ends of thread 343 are tapered for ease of advancing and retracting.

Referring to FIG. 17 and FIG. 22, bushing 351 has a uniform hexagonal aperture 352 the same size as aperture 309 in bushing 307 of stent 301, and a tapered interior wall 353 extended from it's full diameter at it's proximal end to aperture 352. Bushing 351 also has an external tapered tip 354 at it's distal end. Bushing 351 is affixed within the distal end 345 of tube 342 with tip 354 protruding, such that the distal end 345 of stent-follower 341 mates with a self-centering action with the proximal end of stent 301 when the two devices are brought into contact with approximate axial alignment. When stent-follower 341 and stent 301 are thus mated, tip 334 of stylet 331 may be extended through aperture 352 and into aperture 309, thereby locking stent 301 and stent-follower 341 into a fixed rotational relationship. In this condition, the rotation of the proximal end of stylet 331 and stent-follower 341, causes the concurrent rotation of stent 301, whether to rotatingly advance or retract the stent. Stylet 331 may be withdrawn and stent-follower 341 rotatingly retracted, leaving stent 301 positioned at any useful point within a passageway.

Figure 23:
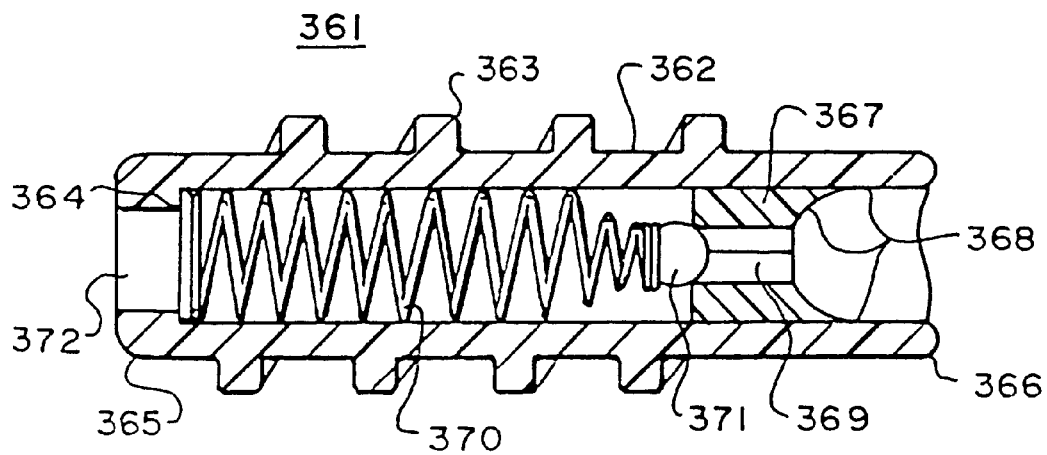
FIG. 23 is a cross section view of a intraurethral catheter with flow control, showing the coiled wall reinforcement member acting as a spring on the ball of the check valve.
Figure 24:
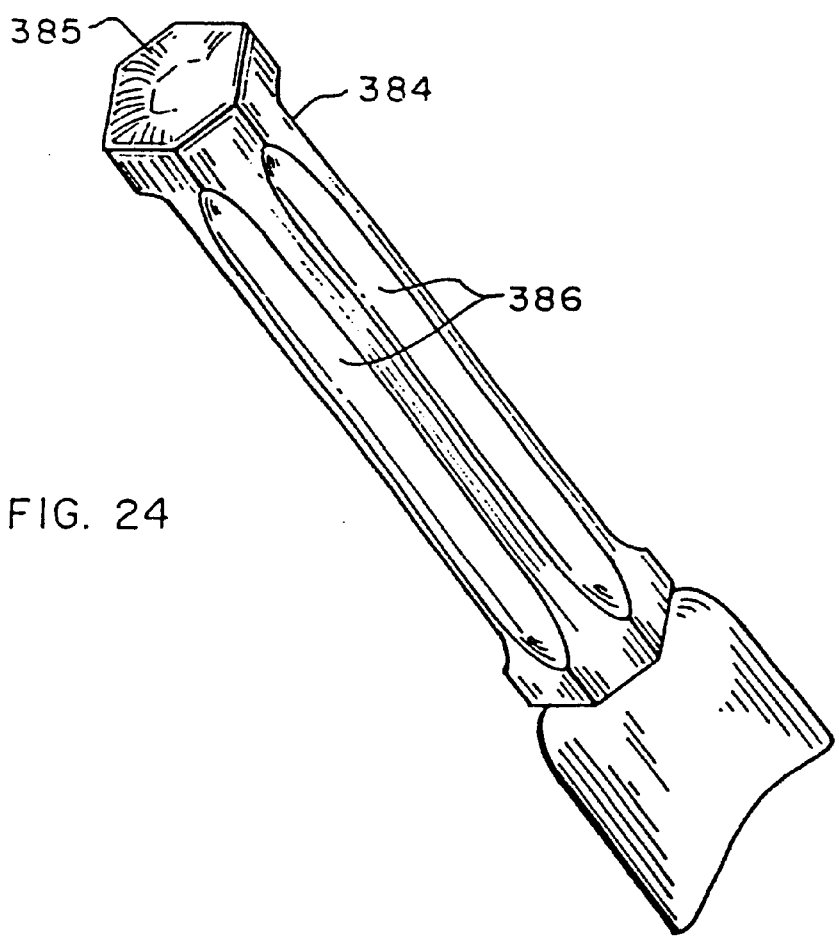
FIG. 24 is a closeup perspective view of a stylet tip for operating the check valve of the intraurethral catheter of FIG. 23.

Referring now to FIG. 23, threaded intraurethral catheter 361, shown in cross section, incorporates means for flow control. The catheter has a tube 362 made from a section of extruded polyurethane tubing material, with thread 363 of uniform pitch and not more than six turns applied to it's external surface. Thread 363 conforms to the same twenty percent (20%) rule of thread height to tube diameter, and ratio of thread pitch to thread circumference of less than one to one (1/1), as thread 103 in FIGS. 2 and 3 as described above.

Alternative embodiments may have a section of the thread being tapered to a lesser height or no height, to provide a "waist" for gripping by a muscular zone such as the prostate or sphincter. Also, reinforcement member 370 could be configured or molded into the sidewall tube 362.

There is an interior shoulder 364 at the distal end 365 of catheter 361, a bushing 367 of relatively harder material with a tapered interior wall 368 extending from the bushing's full diameter at one end to a uniform hexagonal aperture 369, bushing 367 being affixed within the distal end 366 of catheter 361 and oriented with tapered wall 368 extending proximally.

A coiled sidewall reinforcement member 370 and a check ball 371 are secured within the remaining length of catheter 361 by bushing 367 and interior shoulder 364 so that coiled member 370 holds ball 371 in compression against the upper end of bushing 367 in the manner of a check valve, which prevents outward flow through the lumen 372 of the stent. Coiled member 370 may be compressed by upward movement of ball 371, thereby opening the check valve to flow.

Referring to FIGS. 19, 21, 23 and 24, alternate hexagonal tip 384 for stylet 331 has a slightly concave proximal end 385 and flutes 386. When used in conjunction with stent-follower 341 to actuate the check valve of catheter 361, tip 384 is be inserted through aperture 369 of catheter 361 to push ball 371 upward against coil member 370, thereby opening the check valve function and permitting outward flow of fluid through flutes 386 and aperture 369 into and through stent-follower 341.

Suprapubic

Figure 25:
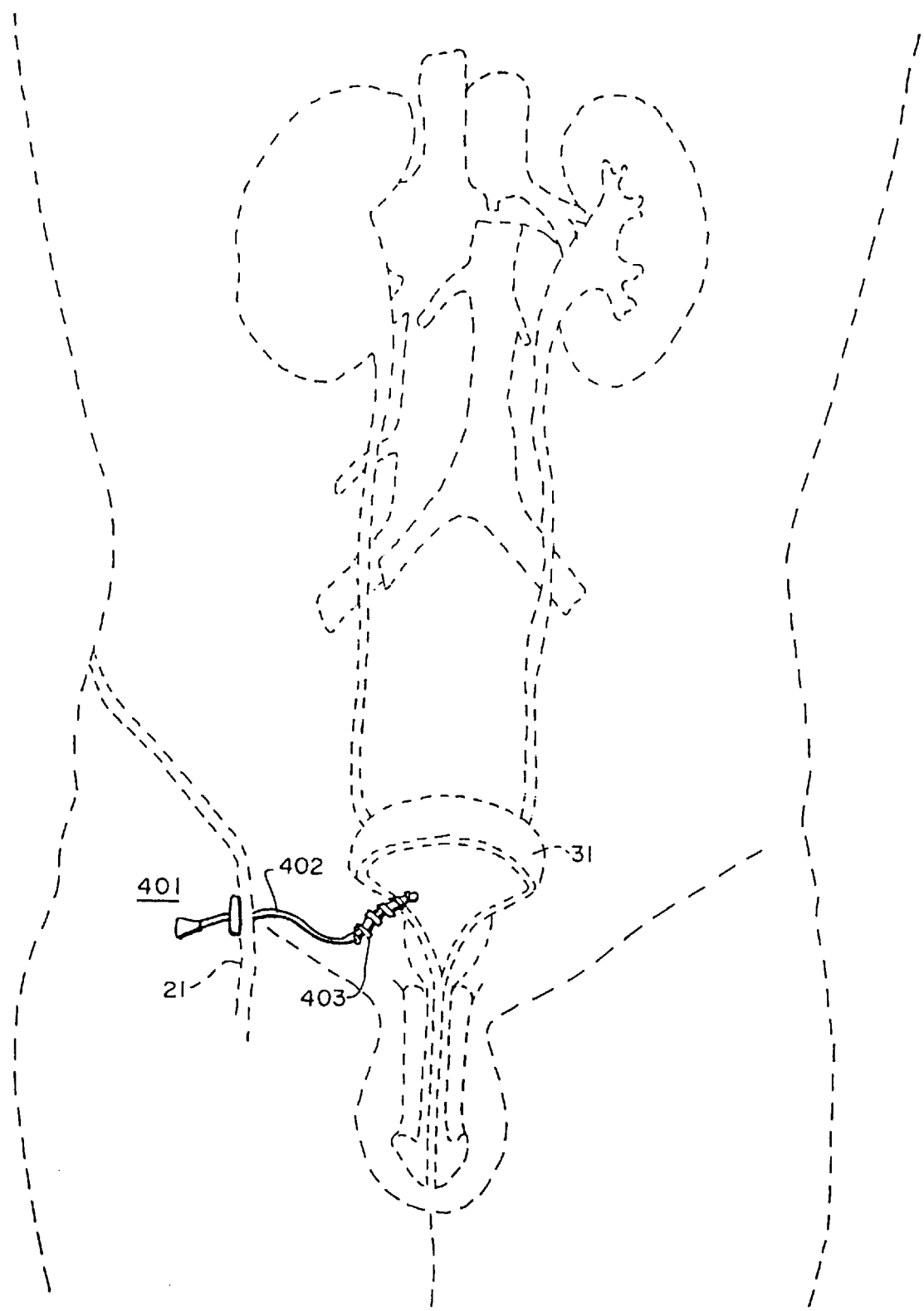
FIG. 25 is a diagrammatic illustration of a suprapubic catheter emplaced through the abdomen with the distal end anchored by it's helical thread in the bladder wall.
Figure 26:
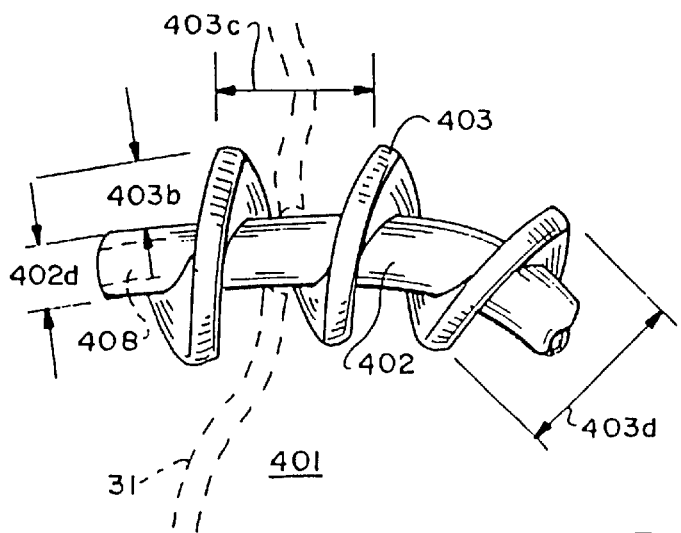
FIG. 26 is a partial side perspective view of the helical thread of the suprapubic catheter of FIG. 25, anchored by it's helical thread in a hole in the bladder wall.

Referring now to FIGS. and 25–29, the threaded suprapubic catheter 401 of FIGS. 25 and 26 is constructed with a flexible tube 402 with a lumen 408 connecting axial ports at the proximal end and the distal end, and an external thread 403 of uniform pitch applied at it's distal end. As described for catheter 101 of FIGS. 2 and 3, the ratio of thread pitch 403c to the circumference of thread diameter 403d is much less than one to one (1/1). Tube 402 is of sufficient torsional strength to accept and transmit rotational finger force applied at the proximal end to the distal end. The ends of 403 are tapered for ease of advancing and retracting the catheter through the abdomen and into the bladder wall.

Figure 27:
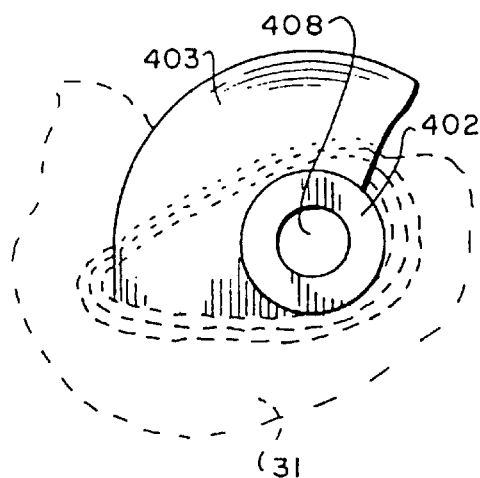
FIG. 27 is a partial front perspective of the suprapubic catheter of FIGS. 25 and 26 anchored in a hole in the bladder wall; the hole being stretched and deformed to fit tightly about the tube and thread of the catheter.

Referring to FIGS. 26 and 27, relative thread height 403b, as a percentage of tube diameter 402d, is necessarily much greater than in the case of catheter 101 of FIGS. 2 and 3; greater than fifty percent (50%). The suprapubic catheter is being advanced by the rotation of thread 403 along an unlined path through the abdomen, and being anchored against longitudinal displacement by the low pitch 403c of thread 403 as to it's circumference in a hole pierced into organ wall 031 that must encompass tube 402 plus thread 403 passing through the plane of the organ wall 031. This is distinguished from the longer gripping surface available in a lined passage way as is the case for catheter 101 of FIG. 4.

Figure 28:
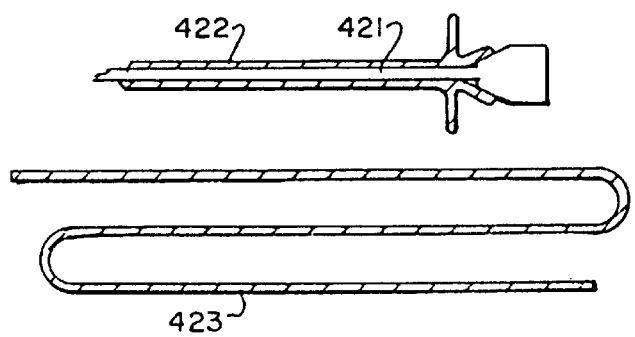
FIG. 28 is a diagrammatic view of a trocar, cannula and guide wire, used to install the suprapubic catheter of FIG. 25.

Referring to FIG. 28, a method by which suprapubic catheter 401 is applied is conventional to the extent that trocar 421 and cannula 422 are used with ultrasound or fluoroscopy to create the path through abdomen wall 021 into the bladder organ 031; trocar 421 is removed and temporary guide wire 423 is then inserted through cannula 422, extending from outside the abdomen wall 021 to inside the bladder organ 031. Cannula 422 is then withdrawn, leaving guidewire 423 as a connecting path extending from outside the body, passing through the abdominal wall 021, and into the bladder organ 031.

Suprapubic catheter 401 is then threaded through it's axial ports onto the proximal end of guide wire 423, and gently started into the abdomen wall 021 with a rotating motion about one turn until thread 403 is firmly engaged. The catheter is then rotatingly advanced along the guide wire through the unlined pathway in the same manner as other threaded devices of the invention, until thread 403 penetrates the wall of organ 031 about one full turn, as determined by ultrasound, fluoroscopy or equivalent means. The distal end of catheter 401 is secured in a non-rotatable fashion to abdomen wall 021 using conventional adhesive means or equivalent means, thereby locking thread 403 at the distal end of the catheter in position in the wall of organ 031. Guide wire 423 is withdrawn. Threaded suprapubic catheter 401 is then available for use.

Figure 29:
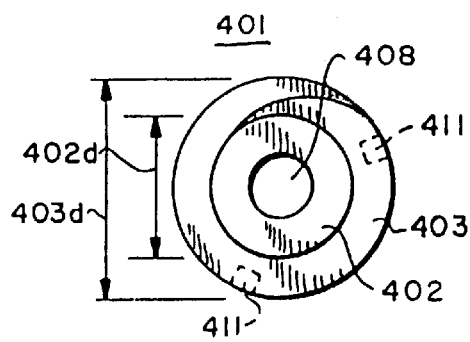
FIG. 29 is a distal end view of the suprapubic catheter of FIG. 21, showing rotational orientation markers.

Referring to FIG. 29, radiopaque markers 411 embedded at select points displaced along the perimeter of thread 403 provide the capability for external detection and monitoring through fluoroscopy or other means of orientation and movement of the distal end of the catheter.

Camera Introducer

Figure 31A:
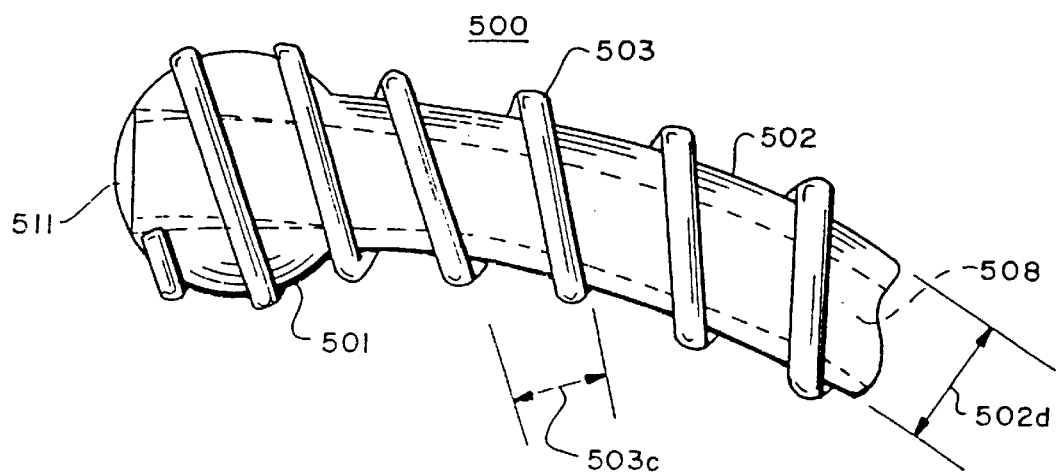
FIG. 31A is a partial front-side perspective of the distal end of the catheter of FIG. 30, showing the larger thread height of the thread in the distal area of the catheter's length.
Figure 30:
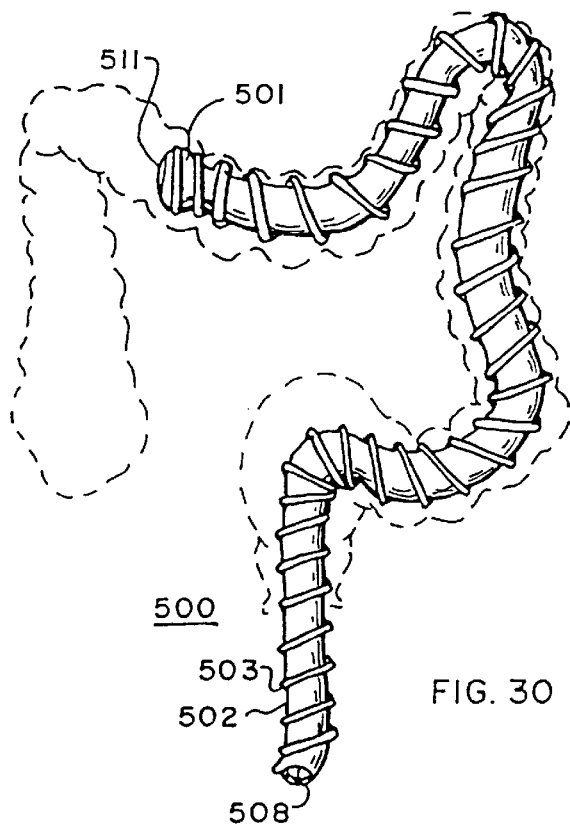
FIG. 30 is a front perspective diagram of a threaded camera introducer catheter advanced into the transverse colon area.

Referring to FIGS. 30 and 31A, threaded camera introducer catheter 500, suitable for an average size adult's colon, consists of a bulbous tip 501 connecting to a soft, flexible tube 502 which is about 5 feet long with a tube diameter 502d of one (1) inch. Lumen 508 extends from the interior face of a window 511 on the distal end of tip 501, through tip 501 and tube 502 to the proximal end of tube 502.

Figure 31B:
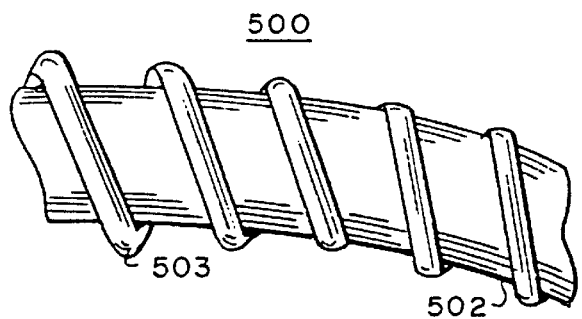
FIG. 31B is a partial side view of the mid section of the catheter of FIG. 30, showing the reduced thread height of the thread in other than the distal area of the catheter's length.

Referring to FIG. 31A, external thread 503 with uniform pitch 503c of 1 inch begins at the edge of window 511, tapering from nothing to a height of about 0.16 inches, extending around tip 501 and tapering there to about 0.32 inches and continuing proximally for about 6 inches along tube 502. Referring to FIG. 31B, thread height then tapers from a thread height of 0.32 inches down to 0.16 inches and continues at this height to the proximal end of tube 502.

An alternative embodiment of the introducer 500 may have a relatively diminutive tip, but maintain an external thread of equal or greater height and total circumference. Another variation of introducer 500 may have thread 503 applied only to it's distal end, the thread terminating after a few turns, analogous to catheter 101 of FIG. 2.

It is readily apparent from the dimensions of FIGS. 31A and B that the 0.32 inch thread height of thread 503 spanning about 6 inches at the distal end of camera introducer 500 is greater than twenty percent (20%) of tube diameter 502d. A relative thread height in the range of 20 percent or more of the camera introducer diameter size appropriate to the subject's size, is necessary to expand and penetrate the walls of the colon to a sufficient depth to achieve a useful grip by the thread in accordance with the rotate to advance technology of the invention. The relatively lower thread height of the continuing thread is adequate to assist in the rotational advancement of the full length of the device without exerting undue forward pressure on the distal end. It also aids in the easing of advancement over the full length of the introducer around and through the bends in the colon.

It will be further apparent, consistent with the techniques, structure and methodology of the invention, that the thread pitch 503c, at one inch, is much less than the overall circumference of thread 503, thereby providing the necessary leverage to translate rotational effort at the proximal end to a forward force significantly greater than the perpendicular scrapping force against the wall of the colon. Simple vector analysis confirms this result.

Figure 32:
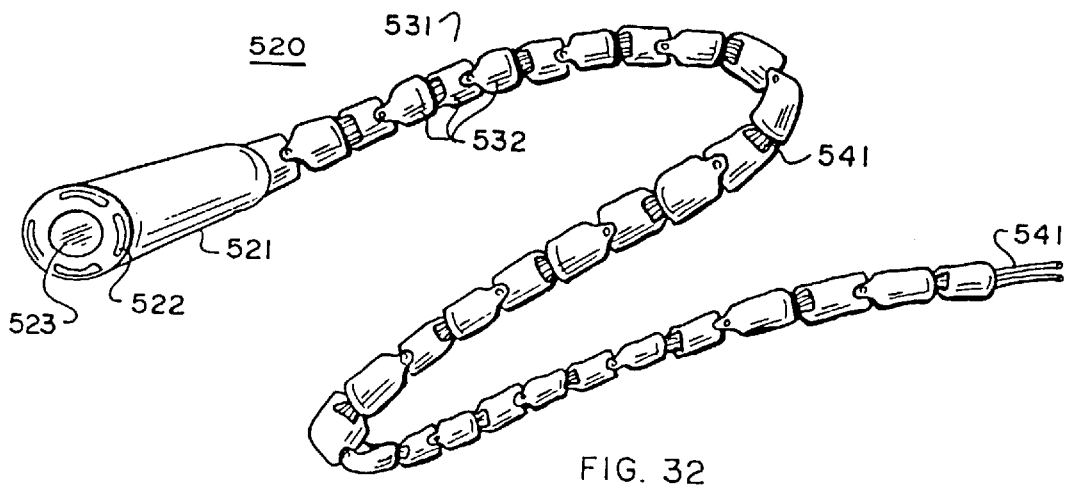
FIG. 32 is a perspective view of a camera assembly with a video camera or visual sensor head attached to a flexible torque tube or assembly within which run electrical cables and/or light bundles.

Referring to FIG. 32, a camera assembly 520 consists of camera 521 with light lens 522 and image lens 523, attached to a flexible, hollow, jointed spine 531. A cable harness 541 connected to camera 521, passes through spine 531, extending out the proximal end and connecting to the necessary power, control and display equipment. Spine 531 is constructed of a chain of vertebrae 532, connected by universal joints which combine flexibility with torsional strength.

Figure 33:
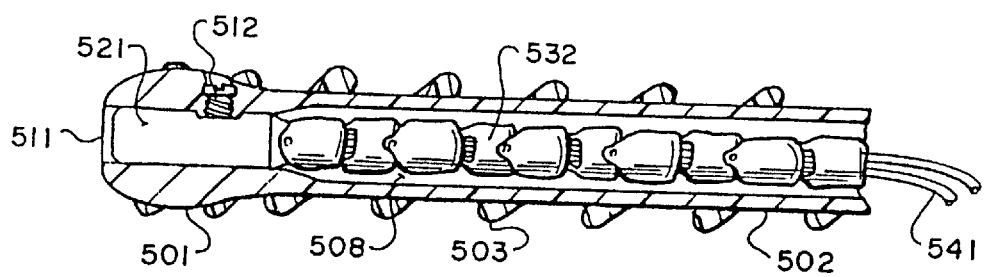
FIG. 33 is a partial cross section view of the distal end of the preferred embodiment of FIG. 1, with the camera assembly of FIG. 2 installed as it would be used, with textual information relating to the construction and use of the device.

Referring to FIG. 33, camera assembly 520 is shown installed in camera introducer catheter 501, with camera 521 secured within tip 501 by set screw 512, so that the camera views forward through the window. The camera assembly and catheter are combined here as a camera introducer system.

Figure 34:
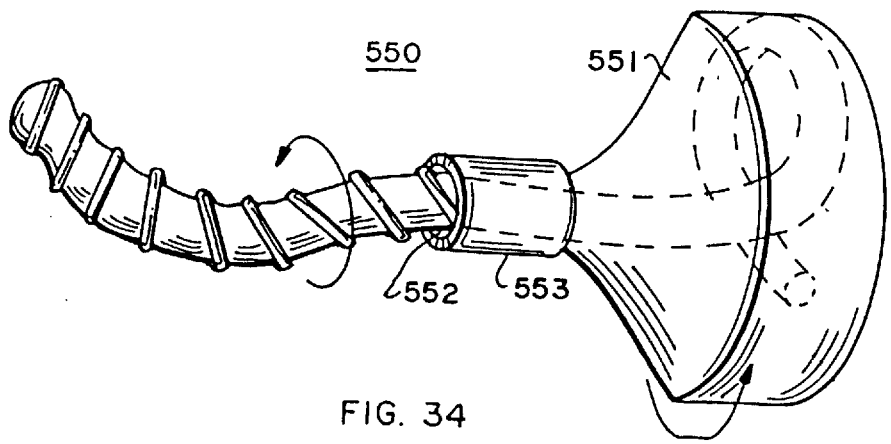
FIG. 34 is a rotating container and dispensing device by which the catheter of FIG. 30 may be managed and administered during it's application to a patient.

Referring to FIG. 34, rotating container and dispensing system 550 consists of drum 551 with axial opening 552 around which handle 553 is rotatably attached. Catheter 501 is rotatingly dispensed during application by holding handle 553 and rotating drum 551 while catheter 401 is being rotatingly advanced in the subject colon.

As will be realized, the invention is capable of other and different embodiments, and its several details are capable of modifications in various obvious respects, all without departing from the invention. The objects and advantages of the invention may be further realized and attained by means of the instrumentalities and combinations particularly pointed out in the appended claims. Accordingly, the drawings and description are to be regarded as illustrative in nature, and not as restrictive.

I claim:

1. A threaded stent for supporting mammalian genitourinary and gastrointestinal passages, said stent comprising a flexible tube with an external helical thread disposed thereon for causing a gentle, gradual displacement of the mammalian genitourinary and gastrointestinal passages without incising or rupturing the same, said tube further comprising means for axial engagement in a non-rotational relationship with the distal end of a stylet, said thread having a thread height of at least one fifth (⅕) of the outside diameter of said tube and a thread pitch not greater than the circumference of an imaginary circle enscribing the outer boundary of said thread.

2. The threaded stent of claim 1, said thread being of uniform pitch.

3. The threaded stent of claim 1, said flexible tube having a distal end and a proximal end, and said flexible tube having a constant diameter from said distal end to said proximal end, wherein said distal end forms a blunt leading end to avoid false passageways.

4. The threaded stent of claim 1, said flexible tube having a distal end and a proximal end, and said thread height being varied along a portion between said distal end to said proximal end so as to form a waist for gripping by a muscular zone including the prostate and the sphincter.

5. The threaded stent of claim 1, said flexible tube further comprising a valve for flow control.

6. A method for supporting mammalian genitourinary and gastrointestinal passages, said method comprising:

providing a threaded stent for supporting mammalian genitourinary and gastrointestinal passages, said stent comprising a flexible tube with an external helical thread disposed thereon for causing a gentle, gradual displacement of the mammalian genitourinary and gastrointestinal passages without incising or rupturing the same, said tube further comprising means for axial engagement in a non-rotational relationship with the distal end of a stylet, said thread having a thread height of at least one fifth (⅕) of the outside diameter of said tube and a thread pitch not greater than the the circumference of an imaginary circle enscribing the outer boundary of said thread; and advancing said threaded stent to a desired portion of one of said mammalian genitourinary and gastrointestinal passages, said advancing being conducted by turning said stent.

* * * * *